US009487753B2

(12) United States Patent
Kukekeov et al.

(10) Patent No.: US 9,487,753 B2
(45) Date of Patent: *Nov. 8, 2016

(54) COMPOSITIONS OF ADULT DISC STEM CELLS AND METHODS FOR THE TREATMENT OF DEGENERATIVE DISC DISEASE

(75) Inventors: Valery Kukekeov, Memphis, TN (US); Christopher Duntsch, Memphis, TN (US); Tatyana Igantova, Memphis, TN (US)

(73) Assignee: DISCGENICS, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/333,549

(22) Filed: Dec. 21, 2011

(65) Prior Publication Data

US 2012/0114713 A1    May 10, 2012

Related U.S. Application Data

(63) Continuation of application No. 12/216,544, filed on Jul. 7, 2008.

(60) Provisional application No. 60/929,792, filed on Jul. 12, 2007.

(51) Int. Cl.
| C12N 5/077 | (2010.01) |
| A61F 2/44 | (2006.01) |
| A61K 35/12 | (2015.01) |

(52) U.S. Cl.
CPC ............. *C12N 5/0655* (2013.01); *A61K 35/12* (2013.01); *C12N 2500/25* (2013.01); *C12N 2500/46* (2013.01); *C12N 2500/90* (2013.01); *C12N 2501/11* (2013.01); *C12N 2501/115* (2013.01); *C12N 2501/392* (2013.01); *C12N 2533/54* (2013.01); *C12N 2533/78* (2013.01)

(58) Field of Classification Search
CPC .... A61K 35/12; A61K 35/42; A61K 9/0073; C12N 2501/11; C12N 2501/115; C12N 5/0655; C12N 2500/25; C12N 2500/46; C12N 2500/90; C12N 2501/392; C12N 2533/54; C12N 2533/78; C12N 2501/117
See application file for complete search history.

(56) References Cited

U.S. PATENT DOCUMENTS

| 4,655,777 A | 4/1987 | Dunn et al. |
| 4,693,721 A | 9/1987 | Ducheyne |
| 4,772,287 A | 9/1988 | Ray et al. |
| 4,904,260 A | 2/1990 | Ray et al. |
| 4,911,718 A | 3/1990 | Lee et al. |
| 4,990,163 A | 2/1991 | Ducheyne et al. |
| 5,002,576 A | 3/1991 | Fuhrmann et al. |
| 5,007,939 A | 4/1991 | Delcommune et al. |
| 5,035,713 A | 7/1991 | Friis |
| 5,041,138 A | 8/1991 | Vacanti et al. |
| 5,074,916 A | 12/1991 | Hench et al. |
| 5,084,051 A | 1/1992 | Tormala et al. |
| 5,108,438 A | 4/1992 | Stone |
| 5,171,326 A | 12/1992 | Ducheyne et al. |
| 5,204,104 A | 4/1993 | Bolinger et al. |
| 5,258,043 A | 11/1993 | Stone |
| 5,290,552 A | 3/1994 | Sierra et al. |
| 5,366,508 A | 11/1994 | Brekke |
| 5,376,118 A | 12/1994 | Kaplan et al. |
| 5,376,120 A | 12/1994 | Sarver et al. |
| 5,458,642 A | 10/1995 | Beer et al. |
| 5,468,544 A | 11/1995 | Marcolongo et al. |
| 5,478,739 A | 12/1995 | Slivka et al. |
| 5,591,453 A | 1/1997 | Ducheyne et al. |
| 5,643,789 A | 7/1997 | Ducheyne et al. |
| 5,645,934 A | 7/1997 | Marcolongo et al. |
| 5,648,301 A | 7/1997 | Ducheyne et al. |
| 5,676,720 A | 10/1997 | Ducheyne et al. |
| 5,686,091 A | 11/1997 | Leong et al. |
| 5,721,049 A | 2/1998 | Marcolongo et al. |
| 5,811,302 A | 9/1998 | Ducheyne et al. |
| 5,817,327 A | 10/1998 | Ducheyne et al. |
| 5,830,480 A | 11/1998 | Ducheyne et al. |
| 5,849,331 A | 12/1998 | Ducheyne et al. |
| 5,861,176 A | 1/1999 | Ducheyne et al. |
| 5,871,777 A | 2/1999 | Ducheyne et al. |
| 5,874,109 A | 2/1999 | Ducheyne et al. |
| 5,964,807 A | 10/1999 | Gan et al. |

(Continued)

FOREIGN PATENT DOCUMENTS

| CA | 2311763 | 1/2004 |
| JP | 2001-524307 | 12/2001 |

(Continued)

OTHER PUBLICATIONS

Okuma et al. (2000) Reinsertion of stimulated nucleus pulposus cells retards intervertebral disc degeneration: an in vitro and in vivo experimental study. J. Orthopaedic Research 18: 988-997.*
Gruber et al ( Experimental Cell research 235, 13-21, 1997.*
Duntsch et al (J Stem Cell Res Ther, 2014, 4(11) and 1-8.*
Healy, et al., Hydration and preferential molecular adsorption on titanium in vitro, Biomaterials, 1992, 13(8), 553-561.
McMillin, C.R., et al., "Artificial spinal discs with up to five years follow-up," 20th Annual Meeting of the Society of Biomaterials, Apr. 5-9, 1994, p. 89.
Oiu, Q., et al., "Bone growth on sol-gel calcium phosphate thin films in vitro," Cells and Materials, 1993, 3(4), 351-360.
Risbud et al., Evidence for Skeletal Progenitor Cells in the Degenerate Human Intervertebral Disc. SPINE, 2007, vol. 32, No. 23, pp. 2537-2544.

(Continued)

*Primary Examiner* — Anoop Singh
(74) *Attorney, Agent, or Firm* — Dorsey & Whitney LLP

(57) ABSTRACT

This invention provides an isolated disc stem cell population, compositions, and methods of obtaining and growing the same. Moreover, this invention provides an isolated discosphere, compositions, and methods of obtaining and growing the same. An artificial disc containing the cells of the present invention is provided together with methods of making the same. This invention also provides a method of treating a subject having a herniated disc utilizing the cells and methods of the invention.

7 Claims, 3 Drawing Sheets

(56) References Cited

U.S. PATENT DOCUMENTS

| | | | |
|---|---|---|---|
| 6,080,579 | A | 6/2000 | Hanley, Jr. et al. |
| 6,121,172 | A | 9/2000 | Marcolongo et al. |
| 6,197,586 | B1 | 3/2001 | Bhatnagar et al. |
| 6,224,913 | B1 | 5/2001 | Ducheyne et al. |
| 6,240,926 | B1 | 6/2001 | Gan et al. |
| 6,328,990 | B1 | 12/2001 | Ducheyne et al. |
| 6,340,369 | B1 | 1/2002 | Ferree |
| 6,413,538 | B1 | 7/2002 | Garcia et al. |
| 6,489,165 | B2 | 12/2002 | Bhatnagar et al. |
| 7,101,545 | B1 | 9/2006 | Hanley, Jr. et al. |
| 7,445,776 | B2 | 11/2008 | Hanley, Jr. et al. |
| 2001/0014355 | A1 | 8/2001 | Ducheyne et al. |
| 2001/0020476 | A1 | 9/2001 | Gan et al. |
| 2003/0165473 | A1 | 9/2003 | Masuda et al. |
| 2003/0220692 | A1* | 11/2003 | Shapiro et al. ............ 623/17.16 |
| 2004/0034427 | A1* | 2/2004 | Goel et al. ................ 623/17.16 |
| 2004/0241839 | A1 | 12/2004 | Svetlov et al. |
| 2007/0110729 | A1 | 5/2007 | Kang et al. |
| 2007/0292414 | A1 | 12/2007 | Duntsch et al. |
| 2009/0074835 | A1 | 3/2009 | Kukekeov et al. |

FOREIGN PATENT DOCUMENTS

| | | | |
|---|---|---|---|
| WO | WO 95/05083 | | 2/1995 |
| WO | WO 98/05274 | | 2/1998 |
| WO | WO99/27077 | * | 6/1999 |
| WO | WO 99/27077 | | 6/1999 |
| WO | 2008/136733 A1 | | 11/2008 |

OTHER PUBLICATIONS

Anonymous, Generalized intervertebral disk degeneration throughout the lumbar spine with secondary osteoarthritis, *International Surgery*, Compere, E.L., Moderator, Sep. 1968,50(3),222-241.

Baldick, H., et al., "Bioactive glass increases alkaline phosphatase activity in rat marrow stromal cells in vitro" *Transactions 5th World Biomaterials Conference*, Toronto, Canada, May 29-Jun. 1996, pace 114.

Boden, S.D., et al., "Abnormal magnetic-resonance scans of the lumbar spine in asymptomatic subjects," *J. Bone Joint Surg.*, Mar. 1990, 72A(3), 403-408.

Brink, M_, et al., "Compositional dependence of bioactivity of glasses in the system Na20—K20—MgO—CaO—B203—P20s—Si02," *J. Biomed Master Res.*, Oct. 1997,37(1), 114-121.

Cheng, X.G., etal., RadiologiCal prevalence of lumbar intervertebral disc calcification in the elderly: an autopsy study, *Skeletal Radiology*, 1996,25,231-235.

Ducheyne, P., "Bioglass coatings and bioglass composites as implant materials," *J. Biomedical Materials Res.*, 1985,19,273-291.

El-Ghannam, et al., "Bioactive material template for-in vitro synthesis of bone," *J.Biomed. Mat. Res.*, 1995,29,359-370.

Fujiwara, A., et al., "The relationship between facet joint osteoarthritis and disc degeneration of the lumbar spine: an MRI study," *European Spine Journal*, 1999, 8, 396-401.

Gao, H., et al., "Surface transformation of bioactive glass in bioreactors simulating microgravity conditions. Part II: numerical simulations," *Biotechnology and Bioengineering*, Nov. 5, 2001, 75(3), 379-385.

Grazier, K.L. (Ed.), The Frequency of Occurrence, Impact and Cost of Musculoskeletal Conditions in the United States, ' 1984.

Hedman, et al., "Design of an intervertebral disc prosthesis," *Spine*, 1991,16 (Supp. 6),256-260.

Krtolica. A., et al., "Hypoxia arrests ovarian carcinoma cell cycle progression, but invasion is unaffected," *Cancer Res.*, 1996, 56(5), 1168-1173.

Lee, C, et al., "Development ofa prosthetic intervertebral disc"j*Spine*, '1991, 16(6 Suppl) , 8253-S255.

Lee, et al., 35th Annual Meeting of the Orthopaedic Research Society, Las Vegas, Nevada, Feb. 6-9, 1989, p. 353.

Lehmann, T.R., et al., "Long-term follow-up of lower lumbar fusion patients," *Spine*, 1987, 12(2)104,97.

Maldonado, B.A., et al., "Initial characterization of the metabolism of intervertebral disc cells encapsulated in microspheres," *J. Orthopaedic Research*, 1992,10,677-690.

Maroudas, "Nutrition and metabolism of the intervertebral disc," *The Biology of the Intervertebral Disc, CRC Press*, 1988, Ghosh, P. (Ed.), Chapter 9, vol. II, 1-37.

Milgram, J.W., "Osteoarthritic changes at the severely degenerative disc in humans," *Spine*, 1982, 7(5), 498-505.

Miller, J.A.A., et al., "Lumbar disc degeneration: correlation with age, sex, and spine level in 600 autopsy specimens," *Spine*, 1988,13(2), 173-178.

Poiraudeau, S., et al., "Phenotypic characteristics of rabbit intervertebral disc cells," *Spine*, May 1, 1999,24(9), 837-844.

Radin, S., et al., "Surface transformation of bioactive glass in bioreactors simulating microgravity conditions. Part I: experimental study," *Biotechnology and Bioengineering*, Nov. 5, 2001, 75(3}, 369-378.

Sabolinski, "Cultured skin as a 'smart material' for healing wounds: experience in venous ulcers," *Biomaterials*, 1996,17,311-320.

Schepers, et al., "Bioactive glass particulate material as a filler for bone lesions," *J. Oral Rehab.*, 1991,18,439-452.

Sedowofia, KA, et al., "Collagenolytic enzyme systems in human intervertebral disc," *Spine*, 1982,7(3),213-222.

Svensson, H-O, et al., "Low-back pain in 40- to 47-year-old-men: work history and work environment factors," *Spine*, 1983,8(3),272-276.

Hou, T.S., et al., "Lumbar intervertebral disc prosthesis," *Chinese Med. J*, 1991, 104(5),381-386.

Trout, J,J et al., "Ultrastructure of the human intervertebral disc: II. cells of the nucleus pulposus," The Anatomical Record, 1982,204,307-314.

Urban, J., "The chemistry of the intervertebral disc in relation to its physiological function and requirements," *Clin. Rheum. Disc.*, Apr. 1980,6(1), 51-77.

Urbaniak, et al., "Replacement of intervertebral discs in chimpanzees by silicone-dacron implants: a preliminary report," Bio. *J. Med. Mater. Res. Sym.*, 1973,4,165-168.

Weisel, S.A., et al., "A study of computer-assisted tomography, 1. The incidence of positive CAT scans in an asymptomatic group of patients," *Spine*, 1984,9, p. 549.

White, et al., "Clinical Biomechanics of the Lumbar Spine," *Churchill Livingston*, London, 1989.

Pattison, S,T., et al., "Regulation of gelatinase-A (MMP-2) production by ovine intervertebral disc nucleus pulposus cells grown in alginate bead culture by transforming growth factor-pi and insulin like growth factor-I," *Cell Biology International*, 2001,25(7), 679-689.

Gruber H, et al., "Autologous Intervertebral Disc Cell Implantation: A Model Using Psammomys obesus, the Sand Rat"; Spine: Aug. 1, 2002—vol. 27—Issue 15—pp. 1626-1633.

Ganey T, et al., "se Chondrocyte Transplantation in a Canine Model: A Treatment for Degenerated or Damaged Intervertebral Disc," Spine: Dec. 1, 2003—vol. 28—Issue 23—pp. 2609-2620.

Risbud M, et al., "Stem cell regeneration of the nucleus pulposus," The Spine Journal; vol. 4, Issue 6, Supplement, pp. S348-S353 (Nov. 2004).

Risbud M, et al., "Differentiation of Mesenchymal Stem Cells Towards a Nucleus Pulposus-like Phenotype In Vitro: Implications for Cell-Based Transplantation Therapy," SPINE vol. 29, No. 23, pp. 2627-2632. Dec. 2004.

Sobashima et al., "Plasticity of cells derived from intervertebral disc nucleus pulposus", The Journal of Japanese Orthopaedic Surgical Society, 2005, vol. 79, No. 8, p. S932.

Ellman et al. Biological impact of the fibroblast growth factor family on articular cartilage and intervertebral disc homeostasis. Gene. 420:82-89. Aug. 15, 2008. [retrieved on Jun. 5, 2012]. Retrieved from Internet: <URL: http://www.ncbi.nlm.nih.gov/pmc/articles/PMC2525607/pdf/n1hms60439.pdf> entire document.

* cited by examiner

COMPOSITIONS OF ADULT DISC STEM CELLS AND METHODS FOR THE TREATMENT OF DEGENERATIVE DISC DISEASE

CROSS REFERENCE TO RELATED APPLICATIONS

This application is a continuation of U.S. patent application Ser. No. 12/216,544, filed Jul. 7, 2008, issued as U.S. Pat. No. 8,227,246 on Jul. 24, 2012, which claims the benefit of U.S. Provisional Application Ser. No. 60/929,792, filed Jul. 12, 2007, which are hereby incorporated by reference in their entirety.

FIELD OF INVENTION

This invention provides: nucleus pulposus stem cells and methods of obtaining and growing the same.

BACKGROUND OF THE INVENTION

Back pain resulting from degenerative disc disease is a major cause of morbidity, disability, and lost productivity. Back pain is the most frequent cause of activity limitation in people under the age of 45, the second most frequent reason for physician visits, the fifth-ranking reason for hospitalization, and the third most common reason for surgical procedures. Additionally, chronic back conditions that are both common and debilitating occur in 15 to 45 percent of people each year, and in 70 to 85 percent of people at some time in their lives. The financial impact in terms of health care dollars and lost work hours to society is between $20 billion and $50 billion per year in the United States alone.

Despite the continued improvements in non-operative and operative treatment options for patients with lower back pain secondary to degenerative disc disease, no treatment modalities have served as the "magic bullet" to eliminate or consistently improve this condition. Today, however, there are new and exciting opportunities for the development of treatment modalities derived from the merging of biomedical engineering and molecular science. We are closer today then ever before to creating new treatment modalities and devices for the treatment of degenerative disc disease. Recent examples of advancements in bioscience and the effect on clinical spine disease include the development of fusion proteins, total disc arthroplasty and more recently nucleus arthroplasty. Fusion proteins, such as recombinant human bone morphogenetic protein-2 (rhBMP-2), are genetically produced proteins that have the ability to stimulate new bone growth to allow for a more reliable and rapid fusion of spinal vertebrae in the context of surgical reconstruction.

The first total disc arthroplasty was performed by Fernstorm in the late 1950's. Although initially there was a short period of symptom relief, the prosthesis ultimately failed secondary to subsidence of the implant within the spine verebra. Although total disc arthroplasty for the lumbar spine has been performed in Europe since the late 1980's, its use in the United States did not begin until March of 2000 with the introduction of the SB Charité III (DePuy Spine, Raynham, Mass.). 10,11 Several other lumbar spine prostheses have since been introduced, including the Maverick (Medtronic Sofamor Danek, Memphis, Tenn.), the Pro-Disc-L (Spine Solutions/Synthes, Paoli, Pa.), and FlexiCore (Stryker Spine, Allendale, N.J.). Each of these prostheses differs in design with respect to bearing surface, fixation to bone, number of articulations, material, constraint, and mobility of the center of rotation. In addition to the lumbar disc arthroplasty, as of last year trials for cervical disc arthroplasty have begun in the United States. Models of cervical disc arthroplasty include the Bryan Cervical Disk (Medtronic Sofamor Danek), the Prestige ST (Medtronic Sofamor Danek), the Porous Coated Motion artificial cervical disk (Cervitech, Rockaway, N.J.), and the ProDisc-C (Spine Solutions/Synthes).

Nucleus arthroplasty or nucleus replacement devices for degenerative spine disease such as the PDN® Prosthetic Disc Nucleus are similar in concept to TDA and have shown successful results. The PDN® device consists of a hydrogel core center encased in a polyethylene sleeve which shrinks and swells during normal loading and unloading allowing for restoration of disc space height and thus mimicking healthy human disc.

Although the total disc arthroplasty and nucleoplasty may serve as an alternative to interbody spinal fusion, the procedure is not without its complications. The most common complications include adjacent level spinal disease, subsidence, and facet joint arthrosis. Furthermore, recent studies from clinical trials have demonstrated incidences of infection, vertebral body fracture, implant malposition, subsidence, mechanical failure, and paravertebral heterotopic ossification. More serious complications, including anterior dislocation of the implant, have been reported. Also, the issue of wear particles from the total disc arthroplasty (TDA) and the potential effects on the spinal cord are still not known. It is therefore evident that although the development of the total disc arthroplasty is a step forward in the treatment of degenerative disc disease, the ultimate goal should be the development and replacement of a degenerative disc with a new biologic disc which does not have the complications associated with mechanical parts.

More than one million spine surgery procedures are performed annually in United States. Furthermore, the lumbar fusion segment of the spine surgery market is estimated at well over $1 billion in annual revenue.

SUMMARY OF THE INVENTION

This invention provides, in one embodiment, an isolated disc stem cell population.

In another embodiment, the present invention provides a method of isolating disc stem cells, comprising the steps of plating a disc stem cell in a serum free media and producing a discosphere comprising nucleus pulposus cells, thereby isolating disc stem cells.

In another embodiment, the present invention provides a composition comprising disc stem cells In another embodiment, the present invention provides an isolated discosphere.

In another embodiment, the present invention provides a composition comprising a discosphere.

In another embodiment, the present invention provides an artificial disc comprising nucleus pulposus cells.

In another embodiment, the present invention provides a method of producing an artificial disc, comprising the step of growing discospheres in a disc scaffold, thereby producing a spinal disc replacement device.

In another embodiment, the present invention provides a method of treating a subject having a herniated disc, comprising the step of administering to said subject an artificial disc comprising nucleus pulposus cells, thereby treating a subject having a herniated disc.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE INVENTION

Figure 1:
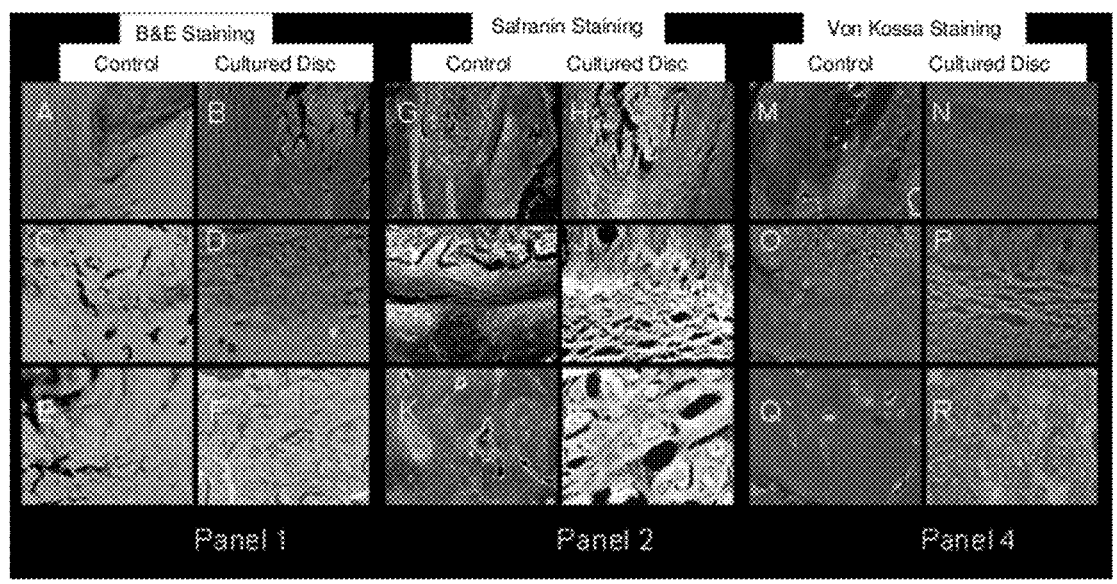
FIG. 1 shows a microscopic histomorphological assessment with various tissue stains of 3 month intervertebral disc cultures after in vitro transplantation of human disc stem cells into evacuated rabbit nucleus pulposus with bony end plates. Panel 1 shows photomicrographs of hematoxylin-eosin staining of rabbit disc tissue in micrographs A, C, and E (control) and cultured intervertebral disc in micrographs B, D, and F. Magnification: 1.25× (A and B), 10× (C and D), and 20× (E and F). Photomicrographs C and D show the transition zone between the inner nucleus pulposus and outer annulus. Photomicrograph E and F show the inner zone of the nucleus pulposus and individual nucleus pulposus cells. Panel 2 shows photomicrographs of safranin staining of rabbit disc tissue in micrographs G, I, and K (control) and cultured intervertebral disc in micrographs H, J, and L. Magnification: 1.25× (G and H), 10× (I and J), and 20× (K and L). Photomicrograph I and J demonstrate the transition zone between the inner nucleus pulposus and outer annulus. Photomicrograph K and L demonstrate the inner zone of the nucleus pulposus and individual nucleus pulposus cells. Panel 3 shows photomicrographs of Von Kossa staining of rabbit disc tissue in micrographs M, O, and Q (control) and cultured intervertebral disc in micrographs H, J, and L. Magnification: 1.25× (M and N), 10× (O and P), and 20× (Q and R). Micrographs O and P demonstrate the transition zone between the inner nucleus pulposus and outer annulus. Micrographs Q and R demonstrate the inner zone of the nucleus pulposus and individual nucleus pulposus cells.

In one embodiment, the present invention provides an isolated disc stem cell population. In another embodiment, the present invention provides a disc stem cells enriched population of cells that can form discospheres. In another embodiment, the present invention provides a disc stem cells enriched population of cells that can give rise to disc progenitor cells. In another embodiment, the isolated disc stem cell population of the present invention comprises a human disc stem cell population. In another embodiment, the isolated disc stem cell population of the present invention comprises a non-human disc stem cell population. In another embodiment, the isolated disc stem cell population of the present invention comprises a mammal disc stem cell population. In another embodiment, an isolated disc stem cell of the present invention is derived from a nucleus pulposus of a subject. In another embodiment, nucleus pulposus cells comprise disc stem cells.

In another embodiment, the stem cells enriched cell population of the present invention comprises a human disc stem cell population. In another embodiment, the stem cells enriched cell population of the present invention comprises a non-human disc stem cell population. In another embodiment, the stem cells enriched cell population of the present invention comprises a mammal disc stem cell population. In another embodiment, the stem cells enriched cell population of the present invention is derived from a nucleus pulposus of a subject. In another embodiment, nucleus pulposus cells comprise disc stem cells.

In another embodiment, a nucleus pulposus is a jelly-like substance in the middle of the spinal disc. In another embodiment, the nucleus pulposus comprises chondrocytes, collagen fibrils, and proteoglycan aggrecans that have hyaluronic long chains which attract water.

In another embodiment, nucleus pulposus cells of the present invention comprise autograft nucleus pulposus cells. In another embodiment, nucleus pulposus cells of the present invention comprise allograft nucleus pulposus cells. In another embodiment, nucleus pulposus cells of the present invention comprise xenograft nucleus pulposus cells.

In another embodiment, nucleus pulposus cells of the present invention comprise disc stem cells. In another embodiment, nucleus pulposus cells of the present invention comprise disc progenitor cells. In another embodiment, nucleus pulposus cells of the present invention comprise mature disc cells. In another embodiment, nucleus pulposus cells of the present invention comprise terminally differentiated disc cells.

In another embodiment, the present invention provides a method of isolating disc stem cells, comprising the step of producing a discosphere culture. In another embodiment, the present invention provides a method of isolating disc stem cells, comprising the step of plating nucleus pulposus cells in a serum free media. In another embodiment, the present invention provides a method of producing a sphere comprising nucleus pulposus cells, comprising the step of growing a culture of nucleus pulposus cells in a serum free media, thereby producing a discosphere. In another embodiment, the present invention provides that a discosphere comprising nucleus pulposus cells is a free-floating structure generated by nucleus pulposus stem cells in vitro. In another embodiment, the present invention provides that a discosphere is a free-floating structure generated by nucleus pulposus progenitor cells in vitro. In another embodiment, the present invention provides that a discosphere is a free-floating structure generated by nucleus pulposus stem and progenitor cells in vitro.

In another embodiment, a disc stem cell of the present invention is defined by its ability or capacity to form a discosphere. In another embodiment, these disc stem cells when grown in adherent culture have the capability to differentiate, under appropriate differentiating conditions, to mature or fully differentiate. In another embodiment, fully differentiated nucleus pulposus cells secrete extra cellular matrix components. In another embodiment, the terms "differentiate" or "differentiation" intended to refer to the development of cells with specialized structure and function from unspecialized or less specialized precursor cells, and includes the development of cells that possess the structure and function of nucleus pulposus cells from precursor cells. In another embodiment, the terms "differentiate" or "differentiation" intended to refer to the development of cells with specialized structure and function from disc stem cells. In another embodiment, the terms "differentiate" or "differentiation" intended to refer to the development of cells with specialized structure and function from disc progenitor cells. In another embodiment, appropriate differentiating conditions comprise a media comprising serum.

In another embodiment, the methods of the present invention provide that disc material is obtained from the nucleus pulposus of a subject. In another embodiment, the methods of the present invention provide that disc material is obtained surgically and processed in the lab to create a single cell suspension of nucleus pulposus cells (Example 1). In another embodiment, the methods of the present invention provide that human disc material is obtained surgically and processed in the lab to create a single cell suspension of nucleus pulposus cells. In another embodiment, the methods of the present invention provide that human nucleus pulposus is obtained surgically and processed in the lab to create a single cell suspension of nucleus pulposus cells.

In another embodiment, a heterogeneous population of nucleus pulposus cells is obtained by scraping a nucleus pulposus of a subject. In another embodiment, heterogeneous population of nucleus pulposus cells comprises disc stem cells, disc progenitor cells, and differentiated nucleus pulposus cells. In another embodiment, a heterogeneous population of nucleus pulposus cells is scraped from a nucleus pulposus of a human subject. In another embodiment, the present invention provides that plating a heterogeneous population of nucleus pulposus cells in a serum free media at low cell density results in the survival of nucleus pulposus stem cells. In another embodiment, the term survival of nucleus pulposus stem cells refers to nucleus pulposus stem cells ability to maintain viability under conditions which include a serum-free cell culture media. In another embodiment, the present invention provides that the nucleus pulposus cells (majority of the cells in the tissue) die away because they cannot tolerate serum-free conditions, but the disc stem cells (or nucleus pulposus stem cells, minority of the cells in the tissue) grow into discospheres under theses conditions.

In another embodiment, the present invention provides that plating a heterogeneous population of nucleus pulposus cells in a serum free media at low cell density results in isolation of nucleus pulposus stem cells. In another embodiment, the present invention provides that plating a heterogeneous population of nucleus pulposus cells in a serum free media at low cell density results in enriching a nucleus pulposus cell population for disc stem cells. In another embodiment, the present invention provides that plating a heterogeneous population of nucleus pulposus cells at low cell density in a serum free media, comprising a substance the interferes with cell attachment results in the survival of nucleus pulposus stem cells. In another embodiment, the present invention provides that plating a heterogeneous population of nucleus pulposus cells at low cell density in a serum free media, comprising methylcellulose which interferes with cell attachment, results in the survival of nucleus pulposus stem cells.

In another embodiment, a heterogeneous population of nucleus pulposus cells is obtained from a biopsy specimen of nucleus pulposus minced in pieces. In another embodiment, the pieces are 0.5-10 mm in size. In another embodiment, the pieces are 0.5-20 mm in size. In another embodiment, the pieces are 0.5-3 mm in size. In another embodiment, the pieces are 3-6 mm in size. In another embodiment, the pieces are 6-12 mm in size. In another embodiment, the pieces are 12-20 mm in size. In another embodiment, the pieces are 1-6 mm in size. In another embodiment, the pieces are 3-5 mm in size. In another embodiment, the pieces are 3-4 mm in size (Example 1).

In another embodiment, a heterogeneous population of nucleus pulposus cells is obtained from a biopsy specimen of nucleus pulposus by treating nucleus pulposus with a collagenase II solution (Example 1). In another embodiment, a heterogeneous population of nucleus pulposus cells is obtained from a biopsy specimen of nucleus pulposus by treating nucleus pulposus with a 0.1%-1% clostridial collagenase (Worthington CLS II, 140 u/mg). In another embodiment, a heterogeneous population of nucleus pulposus cells is obtained from a biopsy specimen of nucleus pulposus by treating nucleus pulposus with a collagenase II solution followed by placing the specimen in a shaker thus obtaining a heterogeneous population of nucleus pulposus cells.

In another embodiment, a heterogeneous population of nucleus pulposus cells is obtained from a biopsy specimen of nucleus pulposus by aspiration of a disc of a patient. In another embodiment, a heterogeneous population of nucleus pulposus cells is obtained from a biopsy specimen of nucleus pulposus by aspiration of a disc of a donor animal. In another embodiment, a heterogeneous population of nucleus pulposus cells is obtained from a biopsy specimen of nucleus pulposus by aspiration of a nucleus pulposus of a donor mammal. In another embodiment, a heterogeneous population of nucleus pulposus cells is obtained from a biopsy specimen of nucleus pulposus by aspiration of a healthy disc of a patient.

In another embodiment, the present invention provides a method of producing a discosphere, comprising the step of growing a culture of nucleus pulposus cells in a serum free media, thereby producing a discosphere. In another embodiment, the present invention provides that growing a primary culture of nucleus pulposus cells in a serum free media results in selecting nucleus pulposus stem cells. In another embodiment, the surviving isolated culture of nucleus pulposus stem cells gives rise to discospheres of the present invention. In another embodiment, the surviving disc stem cells enriched culture of nucleus pulposus stem cells gives rise to discospheres of the present invention.

In another embodiment, the supplemented serum free media of the present invention enables only nucleus pulposus stem cells to grow. In another embodiment, the methods of the present invention provide that an enriched nucleus pulposus stem cell population is produced when grown in a growth factor supplemented serum free media of the present invention. In another embodiment, the methods of the present invention provide that an enriched nucleus pulposus stem cell population of the present invention comprises at least 60% nucleus pulposus stem cells. In another embodiment, the methods of the present invention provide that an enriched nucleus pulposus stem cell population of the present invention comprises at least 70% nucleus pulposus stem cells. In another embodiment, the methods of the present invention provide that an enriched nucleus pulposus stem cell population of the present invention comprises at least 80% nucleus pulposus stem cells. In another embodiment, the methods of the present invention provide that an enriched nucleus pulposus stem cell population of the present invention comprises at least 85% nucleus pulposus stem cells. In another embodiment, the methods of the present invention provide that an enriched nucleus pulposus stem cell population of the present invention comprises at least 90% nucleus pulposus stem cells. In another embodiment, the methods of the present invention provide that an enriched nucleus pulposus stem cell population of the present invention comprises at least 95% nucleus pulposus stem cells.

In another embodiment, a discosphere is derived from a single nucleus pulposus stem cell. In another embodiment, only disc stem cells grow when nucleus pulposus cells are plated in a serum free media. In another embodiment, only disc stem cells grow when nucleus pulposus cells are plated at low cell density. In another embodiment, only disc stem cells grow when nucleus pulposus cells are plated at low cell density in a serum free media. In another embodiment, only nucleus pulposus stem cells can grow as free floating solitary cells in the absence of serum.

In another embodiment, the present invention further provides that disc stem cells are grown in a serum free media comprising a compound which inhibits cell maturation. In another embodiment, the present invention further provides that disc stem cells are grown in a serum free media comprising FGF which inhibits cell maturation. In another embodiment, the present invention further provides that disc stem cells are grown in a serum free media comprising a compound that maintains cell juvenility.

In another embodiment, the present invention further provides that disc stem cells are grown in a media comprising a TGF-β superfamily member. In another embodiment, the present invention further provides that disc stem cells are grown in a media comprising a BMP. In another embodiment, the present invention provides that a BMP of the invention inhibits differentiation (Id) genes.

In another embodiment, the present invention further provides that disc stem cells are grown in a media comprising an IL6 cytokine family member. In another embodiment, the present invention further provides that disc stem cells are grown in a media comprising leukemia inhibitory factor (LIF).

In another embodiment, the present invention further provides that disc stem cells are grown in a serum free media comprising a compound which promotes cell proliferation. In another embodiment, the present invention further provides that disc stem cells are grown in a serum free media comprising EGF which promotes cell proliferation. In another embodiment, the present invention further provides that disc stem cells are grown in a serum free media comprising interleukin-2 (IL-2). In another embodiment, the present invention further provides that disc stem cells are grown in a serum free media comprising interleukin-6 (IL-6). In another embodiment, the present invention further provides that disc stem cells are grown in a serum free media comprising a stem cell factor (SCF). In another embodiment, the present invention further provides that disc stem cells are grown in a serum free media comprising leukemia inhibitory factor (LIF). In another embodiment, the present invention further provides that disc stem cells are grown in a serum free media comprising transforming growth factor-β (TGF-β). In another embodiment, the present invention further provides that disc stem cells are grown in a serum free media comprising a compound that inhibits cell differentiation (Example 1 and materials and methods).

In another embodiment, disc stem cells of the present invention proliferate and give rise to additional stem cells. In another embodiment, disc stem cells of the present invention proliferate and give rise to disc progenitor cells. In another embodiment, disc stem cells of the present invention proliferate thus forming a discosphere. In another embodiment, a discosphere of the present invention comprises nucleus pulposus stem cells and nucleus pulposus progenitor cells arranged in a circular-spherical structure. In another embodiment, a discosphere is a ball of cells in which a single disc stem cell gives rise to clones of itself (symmetric division) and to progenitor cells. In another embodiment, a discosphere of the present invention comprises free floating nucleus pulposus stem cells and nucleus pulposus progenitor cells arranged in a circular-spherical structure. In another embodiment, the nucleus pulposus cells comprising a discosphere are attached to each other.

In another embodiment, the terms "nucleus pulposus stem cells" and "disc stem cells" are used interchangeably. In another embodiment, the terms "nucleus pulposus progenitor cells" and "disc progenitor cells" are used interchangeably.

In another embodiment, the term "discosphere" comprises a ball of cells in which a single disc stem cell gives rise to clones of itself (symmetric division) and to progenitor cells. In another embodiment, the term "progenitor cells" refer to immature stem-like cells with plastic potential and high proliferation rates, which can give rise to most if not all terminally differentiated tissue cells, but is not by definition a disc stem cell.

In another embodiment, the methods of the present invention provide that a single cell suspension is prepared for isolating a disc stem cell by creating certain environmental conditions. In another embodiment, the methods of the present invention provide that a single cell suspension is prepared for producing a discosphere by creating certain environmental conditions.

In another embodiment, the methods of the present invention provide that a single cell suspension is incubated in a humidified Incubator at 37° C. In another embodiment, the methods of the present invention provide that a single cell suspension is incubated in a humidified Incubator at 35° C. In another embodiment, the methods of the present invention provide that a single cell suspension is incubated in a humidified Incubator at 36° C. In another embodiment, the methods of the present invention provide that a single cell suspension is incubated in a humidified Incubator at 38° C. In another embodiment, the methods of the present invention provide that a single cell suspension is incubated in a humidified Incubator at 39° C. In another embodiment, the methods of the present invention provide that a single cell suspension is incubated in a humidified Incubator at 40° C. In another embodiment, the methods of the present invention provide that a single cell suspension is incubated in a humidified Incubator at 41° C. In another embodiment, the methods of the present invention provide that a single cell suspension is incubated in a humidified Incubator at 42° C.

In another embodiment, the methods of the present invention provide that a single cell suspension is incubated in an incubator further maintaining 3-8% $CO_2$. In another embodiment, the methods of the present invention provide that a single cell suspension is incubated in an incubator further maintaining 4% $CO_2$. In another embodiment, the methods of the present invention provide that a single cell suspension is incubated in an incubator further maintaining 5% $CO_2$. In another embodiment, the methods of the present invention provide that a single cell suspension is incubated in an incubator further maintaining 6% $CO_2$.

In another embodiment, the methods of the present invention provide that a single cell suspension is incubated in an incubator further maintaining 60-100% humidity. In another embodiment, the methods of the present invention provide that a single cell suspension is incubated in an incubator further maintaining 70-100% humidity. In another embodiment, the methods of the present invention provide that a single cell suspension is incubated in an incubator further maintaining 80-100% humidity. In another embodiment, the methods of the present invention provide that a single cell suspension is incubated in an incubator further maintaining 90-100% humidity. In another embodiment, the methods of the present invention provide that a single cell suspension is incubated in an incubator further maintaining 95-100% humidity.

In another embodiment, the methods of the present invention provide that a single cell suspension is plated at a final density of less than $1 \times 10^6$ cells/ml. In another embodiment, the methods of the present invention provide that a single cell suspension is plated at a final density of less than $5 \times 10^5$ cells/ml. In another embodiment, the methods of the present invention provide that a single cell suspension is plated at a final density of less than $1 \times 10^5$ cells/ml. In another embodiment, the methods of the present invention provide that a single cell suspension is plated at a final density of less than $8 \times 10^4$ cells/ml. In another embodiment, the methods of the present invention provide that a single cell suspension is plated at a final density of about $6 \times 10^4$ cells/ml (Example 1).

In another embodiment, the present invention provides a composition comprising disc stem cells. In another embodiment, the subject invention comprises a composition comprising a population of nucleus pulposus cells enriched for nucleus pulposus stem cells. In another embodiment, the composition further comprises an appropriate environment, such as those described herein, wherein, a disc stem cell can be induced to proliferate and generate disc stem cells progeny. In another embodiment, the term environment in which disc stem cells progeny are placed, refers to the combination of external or extrinsic physical and/or chemical conditions that affect and influence the growth and development of disc stem cells. In another embodiment, the environment can be ex-vivo or in-vivo. In another embodiment, a disc scaffold can serve as an in-vivo environment that induces disc stem cells to generate progeny. In another embodiment, the environment is ex-vivo and comprises disc stem cells placed in cell culture medium in an incubator (Example 1).

In another embodiment, the present invention provides a composition comprising disc stem cells and media. In another embodiment, the media is a serum free media. In another embodiment, the composition comprising disc stem cells further comprises Epidermal Growth Factor (EGF) supplemented to the media. In another embodiment, the composition comprising disc stem cells further comprises 1-10 ng/ml EGF supplemented to the media. In another embodiment, the composition comprising disc stem cells further comprises 1-100 ng/ml EGF supplemented to the media. In another embodiment, the composition comprising disc stem cells further comprises 20-50 ng/ml EGF supplemented to the media. In another embodiment, the composition comprising disc stem cells further comprises 50-100 ng/ml EGF supplemented to the media. In another embodiment, the composition comprising disc stem cells further comprises 5-15 ng/ml EGF supplemented to the media. In another embodiment, the composition comprising disc stem cells further comprises 8-12 ng/ml EGF supplemented to the media.

In another embodiment, the composition comprising disc stem cells further comprises FGF supplemented to the media. In another embodiment, the composition comprising disc stem cells further comprises Fibroblast Growth Factor 2 (FGF2) supplemented to the media. In another embodiment, the composition comprising disc stem cells further comprises 1-100 ng/ml FGF2 supplemented to the media. In another embodiment, the composition comprising disc stem cells further comprises 20-50 ng/ml FGF2 supplemented to the media. In another embodiment, the composition comprising disc stem cells further comprises 50-100 ng/ml FGF2 supplemented to the media. In another embodiment, the composition comprising disc stem cells further comprises 5-15 ng/ml FGF2 supplemented to the media. In another embodiment, the composition comprising disc stem cells further comprises 8-12 ng/ml FGF2 supplemented to the media.

In another embodiment, the composition comprising disc stem cells further comprises insulin supplemented to the media. In another embodiment, the composition comprising disc stem cells further comprises 1-100 μg/ml insulin supplemented to the media (Example 1). In another embodiment, the composition comprising disc stem cells further comprises 20-50 μg/ml insulin supplemented to the media. In another embodiment, the composition comprising disc stem cells further comprises 50-100 μg/ml insulin supplemented to the media. In another embodiment, the composition comprising disc stem cells further comprises 5-15 μg/ml insulin supplemented to the media. In another embodiment, the composition comprising disc stem cells further comprises 8-12 μg/ml insulin supplemented to the media.

In another embodiment, the composition comprising disc stem cells further comprises progesterone supplemented to the media (Example 1). In another embodiment, the composition comprising disc stem cells further comprises 1-200 ng/ml progesterone supplemented to the media. In another embodiment, the composition comprising disc stem cells further comprises 20-200 ng/ml progesterone supplemented to the media. In another embodiment, the composition comprising disc stem cells further comprises 50-150 ng/ml progesterone supplemented to the media. In another embodiment, the composition comprising disc stem cells further comprises 10-100 ng/ml progesterone supplemented to the media. In another embodiment, the composition comprising disc stem cells further comprises 20-80 ng/ml progesterone supplemented to the media. In another embodiment, the composition comprising disc stem cells further comprises 30-50 ng/ml progesterone supplemented to the media.

In another embodiment, the composition comprising disc stem cells further comprises putrescine supplemented to the media (Example 1). In another embodiment, the composition comprising disc stem cells further comprises 1-800 ng/ml putrescine supplemented to the media. In another embodiment, the composition comprising disc stem cells further comprises 1-100 ng/ml putrescine supplemented to the media. In another embodiment, the composition comprising disc stem cells further comprises 100-300 ng/ml putrescine supplemented to the media. In another embodiment, the composition comprising disc stem cells further comprises 300-500 ng/ml putrescine supplemented to the media. In another embodiment, the composition comprising disc stem cells further comprises 500-800 ng/ml putrescine supplemented to the media. In another embodiment, the composition comprising disc stem cells further comprises 150-250 ng/ml putrescine supplemented to the media. In another embodiment, the composition comprising disc stem cells further comprises 180-220 ng/ml putrescine supplemented to the media.

In another embodiment, the composition comprising disc stem cells further comprises transferrin supplemented to the media (Example 1). In another embodiment, the composition comprising disc stem cells further comprises 1-400 ng/ml transferrin supplemented to the media. In another embodiment, the composition comprising disc stem cells further comprises 1-100 ng/ml transferrin supplemented to the media. In another embodiment, the composition comprising disc stem cells further comprises 100-200 ng/ml transferrin supplemented to the media. In another embodiment, the composition comprising disc stem cells further comprises 200-400 ng/ml transferrin supplemented to the media. In another embodiment, the composition comprising disc stem cells further comprises 20-150 ng/ml transferrin supplemented to the media. In another embodiment, the composition comprising disc stem cells further comprises 80-200 ng/ml transferrin supplemented to the media. In another embodiment, the composition comprising disc stem cells further comprises 80-120 ng/ml transferrin supplemented to the media.

In another embodiment, the composition comprising disc stem cells further comprises sodium selenite supplemented to the media (Example 1). In another embodiment, the composition comprising disc stem cells further comprises 1-400 ng/ml sodium selenite supplemented to the media. In another embodiment, the composition comprising disc stem cells further comprises 1-100 ng/ml sodium selenite supplemented to the media. In another embodiment, the composition comprising disc stem cells further comprises 100-200 ng/ml sodium selenite supplemented to the media. In another embodiment, the composition comprising disc stem cells further comprises 200-400 ng/ml sodium selenite supplemented to the media. In another embodiment, the composition comprising disc stem cells further comprises 20-150 ng/ml sodium selenite supplemented to the media. In another embodiment, the composition comprising disc stem cells further comprises 40-180 ng/ml sodium selenite supplemented to the media. In another embodiment, the composition comprising disc stem cells further comprises 40-80 ng/ml sodium selenite supplemented to the media.

In another embodiment, the composition comprising disc stem cells further comprises methylcellulose supplemented to the media (Example 1). In another embodiment, the composition comprising disc stem cells further comprises 0.5-10% methylcellulose supplemented to the media. In another embodiment, the composition comprising disc stem cells further comprises 0.5-3% methylcellulose supplemented to the media. In another embodiment, the composition comprising disc stem cells further comprises 3-5% methylcellulose supplemented to the media. In another embodiment, the composition comprising disc stem cells further comprises 5-8% methylcellulose supplemented to the media. In another embodiment, the composition comprising disc stem cells further comprises 7-10% methylcellulose supplemented to the media. In another embodiment, the composition comprising disc stem cells further comprises 0.5-2.5% methylcellulose supplemented to the media. In another embodiment, the composition comprising disc stem cells further comprises 1-2.5% methylcellulose supplemented to the media. In another embodiment, the composition comprising disc stem cells further comprises 1.5-2.5% methylcellulose supplemented to the media.

In another embodiment, the composition comprising disc stem cells further comprises an antibiotic supplemented to the media (Example 1). In another embodiment, the antibiotic supplemented to the media is penicillin-streptomycin. In another embodiment, the composition comprising disc stem cells further comprises 1000-10000 U/ml penicillin-streptomycin supplemented to the media. In another embodiment, the composition comprising disc stem cells further comprises 1000-3000 U/ml penicillin-streptomycin supplemented to the media. In another embodiment, the composition comprising disc stem cells further comprises 3000-6000 U/ml penicillin-streptomycin supplemented to the media. In another embodiment, the composition comprising disc stem cells further comprises 6000-10000 U/ml penicillin-streptomycin supplemented to the media. In another embodiment, the composition comprising disc stem cells further comprises 3000-8000 U/ml penicillin-streptomycin supplemented to the media. In another embodiment, the composition comprising disc stem cells further comprises 4000-6000 U/ml penicillin-streptomycin supplemented to the media. In another embodiment, the composition comprising disc stem cells further comprises 5000 U/ml penicillin-streptomycin supplemented to the media.

In another embodiment, the composition comprising disc stem cells further comprises KO serum replacer supplemented to the media. In another embodiment, the composition comprising disc stem cells further comprises 0.5-30% KO serum replacer supplemented to the media. In another embodiment, the composition comprising disc stem cells further comprises 5-30% knockout (KO) serum replacer supplemented to the media. In another embodiment, the composition comprising disc stem cells further comprises 3-5% KO serum replacer supplemented to the media. In another embodiment, the composition comprising disc stem cells further comprises 5-15% KO serum replacer supplemented to the media. In another embodiment, the composition comprising disc stem cells further comprises 15-30%

KO serum replacer supplemented to the media. In another embodiment, the composition comprising disc stem cells further comprises 10-20% KO serum replacer supplemented to the media. In another embodiment, the composition comprising disc stem cells further comprises 15-25% KO serum replacer supplemented to the media. In another embodiment, the composition comprising disc stem cells further comprises 20% KO serum replacer supplemented to the media.

In another embodiment, the composition comprising disc stem cells further comprises non-essential Amino Acids supplemented to the media. In another embodiment, the composition comprising disc stem cells further comprises 0.1-10% non-essential Amino Acids supplemented to the media. In another embodiment, the composition comprising disc stem cells further comprises 0.1-1% non-essential Amino Acids supplemented to the media. In another embodiment, the composition comprising disc stem cells further comprises 1-5% non-essential Amino Acids supplemented to the media. In another embodiment, the composition comprising disc stem cells further comprises 5-10% non-essential Amino Acids supplemented to the media. In another embodiment, the composition comprising disc stem cells further comprises 15-30% non-essential Amino Acids supplemented to the media. In another embodiment, the composition comprising disc stem cells further comprises 0.5-1% non-essential Amino Acids supplemented to the media. In another embodiment, the composition comprising disc stem cells further comprises 0.8-1.2% non-essential Amino Acids supplemented to the media. In another embodiment, the composition comprising disc stem cells further comprises 1% non-essential Amino Acids supplemented to the media.

In another embodiment, the composition comprising disc stem cells further comprises L-glutamine supplemented to the media. In another embodiment, the composition comprising disc stem cells further comprises 0.1-10 mM L-glutamine supplemented to the media. In another embodiment, the composition comprising disc stem cells further comprises 0.1-5 mM L-glutamine supplemented to the media. In another embodiment, the composition comprising disc stem cells further comprises 5-10 mM L-glutamine supplemented to the media. In another embodiment, the composition comprising disc stem cells further comprises 5-8 mM L-glutamine supplemented to the media. In another embodiment, the composition comprising disc stem cells further comprises 0.5-2.5 mM L-glutamine supplemented to the media. In another embodiment, the composition comprising disc stem cells further comprises 1.5-3 mM L-glutamine supplemented to the media. In another embodiment, the composition comprising disc stem cells further comprises 0.5-1.5 mM L-glutamine supplemented to the media. In another embodiment, the composition comprising disc stem cells further comprises 0.8-1.2 mM L-glutamine supplemented to the media.

In another embodiment, the composition comprising disc stem cells further comprises b-mercaptoethanol supplemented to the media. In another embodiment, the composition comprising disc stem cells further comprises 0.01-1 mM b-mercaptoethanol supplemented to the media. In another embodiment, the composition comprising disc stem cells further comprises 0.01-0.5 mM b-mercaptoethanol supplemented to the media. In another embodiment, the composition comprising disc stem cells further comprises 0.5-1 mM b-mercaptoethanol supplemented to the media. In another embodiment, the composition comprising disc stem cells further comprises 0.5-0.8 mM b-mercaptoethanol supplemented to the media. In another embodiment, the composition comprising disc stem cells further comprises 00.5-0.25 mM b-mercaptoethanol supplemented to the media. In another embodiment, the composition comprising disc stem cells further comprises 0.15-0.3 mM b-mercaptoethanol supplemented to the media. In another embodiment, the composition comprising disc stem cells further comprises 0.05-0.15 mM b-mercaptoethanol supplemented to the media. In another embodiment, the composition comprising disc stem cells further comprises 0.08-0.12 mM b-mercaptoethanol supplemented to the media.

In another embodiment, the composition comprising disc stem cells further comprises a media comprising Dulbecco's Modified Eagle's Medium (DMEM). In another embodiment, the composition comprising a discosphere further comprises a media comprising DMEM/F12. In another embodiment, the composition comprising disc stem cells further comprises a media comprising Hamm's culture media. In another embodiment, the composition comprising disc stem cells further comprises a media comprising Hamm's/F12 culture media. In another embodiment, the composition comprising disc stem cells further comprises a media comprising ESGRO Complete™ Accutase™. In another embodiment, ESGRO Complete™ Accutase™ is a cell detachment solution of proteolytic and collagenolytic enzymes qualified for use for the detachment of stem cells cultured in serum-free conditions with ESGRO Complete™ Clonal Grade Medium. In another embodiment, 1× Accutase™ enzymes in Dulbecco's PBS comprises 0.5 mM EDTA.4Na and 3 mg/L Phenol. In another embodiment, the composition comprising disc stem cells further comprises a media comprising HEScGRO hES cell medium (Chemicon Temecula, Calif.).

In another embodiment, the composition comprising disc stem cells is used for plating disc stem cells in ultra low attachment plates. In another embodiment, the composition comprising disc stem cells is used for plating disc stem cells in ultra low attachment plates precoated with an anti-adhesive substance. In another embodiment, the anti-adhesive substance is poly 2-hydroxyethyl methacrylate.

In another embodiment, the present invention provides an isolated discosphere. In another embodiment, a disc stem cell of the present invention gives rise to an isolated discosphere. In another embodiment, a discosphere of the present invention is the result of stem cell proliferation which gives rise to additional stem cells and progenitor cells. In another embodiment, a discosphere is formed as a result of disc stem proliferation.

In another embodiment, an isolated discosphere of the present invention comprises nucleus pulposus stem cells and nucleus pulposus progenitor cells arranged in a circular-spherical structure. In another embodiment, an isolated discosphere is a ball of cells in which a single disc stem cell gives rise to clones of itself (symmetric division) and to progenitor cells. In another embodiment, a discosphere of the present invention is a free floating conglomerate of nucleus pulposus stem cells and nucleus pulposus progenitor cells arranged in a circular-spherical structure. In another embodiment, a discosphere culture of the present invention comprises solitary free floating discospheres.

In another embodiment, the methods of the present invention provide that isolating a discosphere of the present invention can be readily preformed by one skilled in the art under a light microscope.

In another embodiment, the methods of the present invention provide that a single cell suspension is prepared for isolating a disc stem cell by plating and incubating a disc stem cell in a serum free media. In another embodiment, the methods of the present invention provide that a single cell suspension is prepared for producing a discosphere by plating and incubating a disc stem cell in a serum free media.

In another embodiment, the present invention provides a method of producing a discosphere, comprising the step of growing a culture of nucleus pulposus cells in a serum free media, thereby producing a discosphere. In another embodiment, the present invention provides that growing a primary culture of nucleus pulposus cells in a serum free media results in selecting nucleus pulposus stem cells. In another embodiment, the remaining isolated culture of nucleus pulposus stem cells gives rise to discospheres of the present invention. In another embodiment, the remaining enriched culture of nucleus pulposus stem cells gives rise to discospheres of the present invention. In another embodiment, discospheres according to the methods of the present invention grow in the compositions of the present invention. In another embodiment, discospheres according to the methods of the present invention grow in the supplemented media of the present invention. In another embodiment, discospheres according to the methods of the present invention grow under conditions which do not permit cell-substrate adhesion. In another embodiment, conditions which do not permit cell-substrate adhesion comprise for example the addition of about 0.2-2% methylcellulose to the cell culture media of the present invention.

In another embodiment, the present invention provides a composition comprising a discosphere. In another embodiment, a composition of the present invention comprises a single discosphere. In another embodiment, a composition of the present invention comprises at least $1 \times 10^2$ discospheres. In another embodiment, a composition of the present invention comprises at least $1 \times 10^3$ discospheres. In another embodiment, a composition of the present invention comprises at least $1 \times 10^4$ discospheres. In another embodiment, a composition of the present invention comprises at least $1 \times 10^5$ discospheres. In another embodiment, a composition of the present invention comprises at least $1 \times 10^6$ discospheres.

In another embodiment, the composition of the present invention comprises a discosphere and media. In another embodiment, the media is a serum free media. In another embodiment, the composition comprising a discosphere further comprises EGF supplemented to the media. In another embodiment, the composition comprising a discosphere further comprises 1-10 ng/ml EGF supplemented to the media. In another embodiment, the composition comprising a discosphere further comprises 1-100 ng/ml EGF supplemented to the media. In another embodiment, the composition comprising a discosphere further comprises 20-50 ng/ml EGF supplemented to the media. In another embodiment, the composition comprising a discosphere further comprises 50-100 ng/ml EGF supplemented to the media. In another embodiment, the composition comprising a discosphere further comprises 5-15 ng/ml EGF supplemented to the media. In another embodiment, the composition comprising a discosphere further comprises 8-12 ng/ml EGF supplemented to the media.

In another embodiment, the composition comprising a discosphere further comprises FGF supplemented to the media. In another embodiment, the composition comprising a discosphere further comprises FGF2 supplemented to the media. In another embodiment, the composition comprising a discosphere further comprises 1-100 ng/ml FGF2 supplemented to the media. In another embodiment, the composition comprising a discosphere further comprises 20-50 ng/ml FGF2 supplemented to the media. In another embodiment, the composition comprising a discosphere further comprises 50-100 ng/ml FGF2 supplemented to the media. In another embodiment, the composition comprising a discosphere further comprises 5-15 ng/ml FGF2 supplemented to the media. In another embodiment, the composition comprising a discosphere further comprises 8-12 ng/ml FGF2 supplemented to the media.

In another embodiment, the composition comprising a discosphere further comprises insulin supplemented to the media (Example 2 and materials and methods). In another embodiment, the composition comprising a discosphere further comprises 1-100 µg/ml insulin supplemented to the media. In another embodiment, the composition comprising a discosphere further comprises 20-50 µg/ml insulin supplemented to the media. In another embodiment, the composition comprising a discosphere further comprises 50-100 µg/ml insulin supplemented to the media. In another embodiment, the composition comprising a discosphere further comprises 5-15 µg/ml insulin supplemented to the media. In another embodiment, the composition comprising a discosphere further comprises 3-7 µg/ml insulin supplemented to the media.

In another embodiment, the composition comprising a discosphere further comprises progesterone supplemented to the media. In another embodiment, the composition comprising a discosphere further comprises 1-200 ng/ml progesterone supplemented to the media. In another embodiment, the composition comprising a discosphere further comprises 20-200 ng/ml progesterone supplemented to the media. In another embodiment, the composition comprising a discosphere further comprises 50-150 ng/ml progesterone supplemented to the media. In another embodiment, the composition comprising disc stem cells further comprises 10-100 ng/ml progesterone supplemented to the media. In another embodiment, the composition comprising disc stem cells further comprises 20-80 ng/ml progesterone supplemented to the media. In another embodiment, the composition comprising disc stem cells further comprises 15-25 ng/ml progesterone supplemented to the media.

In another embodiment, the composition comprising a discosphere further comprises putrescine supplemented to the media. In another embodiment, the composition comprising a discosphere further comprises 1-800 ng/ml putrescine supplemented to the media. In another embodiment, the composition comprising a discosphere further comprises 1-100 ng/ml putrescine supplemented to the media. In another embodiment, the composition comprising a discosphere further comprises 100-300 ng/ml putrescine supplemented to the media. In another embodiment, the composition comprising a discosphere further comprises 300-500 ng/ml putrescine supplemented to the media. In another embodiment, the composition comprising a discosphere further comprises 500-800 ng/ml putrescine supplemented to the media. In another embodiment, the composition comprising a discosphere further comprises 150-250 ng/ml putrescine supplemented to the media. In another embodiment, the composition comprising a discosphere further comprises 140-160 ng/ml putrescine supplemented to the media.

In another embodiment, the composition comprising a discosphere further comprises transferrin supplemented to the media. In another embodiment, the composition comprising a discosphere further comprises 1-400 ng/ml transferrin supplemented to the media. In another embodiment, the composition comprising a discosphere further comprises 1-100 ng/ml transferrin supplemented to the media. In another embodiment, the composition comprising a discosphere further comprises 100-200 ng/ml transferrin supplemented to the media. In another embodiment, the composition comprising a discosphere further comprises 200-400 ng/ml transferrin supplemented to the media. In another embodiment, the composition comprising a discosphere further comprises 20-150 ng/ml transferrin supplemented to the media. In another embodiment, the composition comprising a discosphere further comprises 80-200 ng/ml transferrin supplemented to the media. In another embodiment, the composition comprising a discosphere further comprises 30-70 ng/ml transferrin supplemented to the media.

In another embodiment, the composition comprising a discosphere further comprises sodium selenite supplemented to the media. In another embodiment, the composition comprising a discosphere further comprises 1-400 ng/ml sodium selenite supplemented to the media. In another embodiment, the composition comprising a discosphere further comprises 1-100 ng/ml sodium selenite supplemented to the media. In another embodiment, the composition comprising a discosphere further comprises 100-200 ng/ml sodium selenite supplemented to the media. In another embodiment, the composition comprising a discosphere further comprises 200-400 ng/ml sodium selenite supplemented to the media. In another embodiment, the composition comprising a discosphere further comprises 20-150 ng/ml sodium selenite supplemented to the media. In another embodiment, the composition comprising a discosphere further comprises 40-180 ng/ml sodium selenite supplemented to the media. In another embodiment, the composition comprising a discosphere further comprises 20-40 ng/ml sodium selenite supplemented to the media.

In another embodiment, the composition comprising a discosphere further comprises methylcellulose supplemented to the media. In another embodiment, the composition comprising a discosphere further comprises 0.5-10% methylcellulose supplemented to the media. In another embodiment, the composition comprising a discosphere further comprises 0.5-3% methylcellulose supplemented to the media. In another embodiment, the composition comprising a discosphere further comprises 3-5% methylcellulose supplemented to the media. In another embodiment, the composition comprising a discosphere further comprises 5-8% methylcellulose supplemented to the media. In another embodiment, the composition comprising a discosphere further comprises 7-10% methylcellulose supplemented to the media. In another embodiment, the composition comprising a discosphere further comprises 0.5-2.5% methylcellulose supplemented to the media. In another embodiment, the composition comprising a discosphere further comprises 1-2.5% methylcellulose supplemented to the media. In another embodiment, the composition comprising a discosphere further comprises 0.6-1% methylcellulose supplemented to the media.

In another embodiment, the composition comprising a discosphere further comprises an antibiotic supplemented to the media. In another embodiment, the antibiotic supplemented to the media is penicillin-streptomycin. In another embodiment, the composition comprising a discosphere further comprises 1000-10000 U/ml penicillin-streptomycin supplemented to the media. In another embodiment, the composition comprising a discosphere further comprises 1000-3000 U/ml penicillin-streptomycin supplemented to the media. In another embodiment, the composition comprising a discosphere further comprises 3000-6000 U/ml penicillin-streptomycin supplemented to the media. In another embodiment, the composition comprising a discosphere further comprises 6000-10000 U/ml penicillin-streptomycin supplemented to the media. In another embodiment, the composition comprising a discosphere further comprises 3000-8000 U/ml penicillin-streptomycin supplemented to the media. In another embodiment, the composition comprising a discosphere further comprises 4000-6000 U/ml penicillin-streptomycin supplemented to the media. In another embodiment, the composition comprising a discosphere further comprises 5000 U/ml penicillin-streptomycin supplemented to the media.

In another embodiment, the composition comprising a discosphere further comprises KO serum replacer supplemented to the media. In another embodiment, the composition comprising a discosphere further comprises 0.5-30% KO serum replacer supplemented to the media. In another embodiment, the composition comprising a discosphere further comprises 5-30% KO serum replacer supplemented to the media. In another embodiment, the composition comprising a discosphere further comprises 3-5% KO serum replacer supplemented to the media. In another embodiment, the composition comprising a discosphere further comprises 5-15% KO serum replacer supplemented to the media. In another embodiment, the composition comprising a discosphere further comprises 15-30% KO serum replacer supplemented to the media. In another embodiment, the composition comprising a discosphere further comprises 10-20% KO serum replacer supplemented to the media. In another embodiment, the composition comprising a discosphere further comprises 15-25% KO serum replacer supplemented to the media. In another embodiment, the composition comprising a discosphere further comprises 20% KO serum replacer supplemented to the media.

In another embodiment, the composition comprising a discosphere further comprises non-essential Amino Acids supplemented to the media. In another embodiment, the composition comprising a discosphere further comprises 0.1-10% non-essential Amino Acids supplemented to the media. In another embodiment, the composition comprising a discosphere further comprises 0.1-1% non-essential Amino Acids supplemented to the media. In another embodiment, the composition comprising a discosphere further comprises 1-5% non-essential Amino Acids supplemented to the media. In another embodiment, the composition comprising a discosphere further comprises 5-10% non-essential Amino Acids supplemented to the media. In another embodiment, the composition comprising a discosphere further comprises 15-30% non-essential Amino Acids supplemented to the media. In another embodiment, the composition comprising a discosphere further comprises 0.5-1% non-essential Amino Acids supplemented to the media. In another embodiment, the composition comprising a discosphere further comprises 0.8-1.2% non-essential Amino Acids supplemented to the media. In another embodiment, the composition comprising a discosphere further comprises 1% non-essential Amino Acids supplemented to the media.

In another embodiment, the composition comprising a discosphere further comprises L-glutamine supplemented to the media. In another embodiment, the composition comprising a discosphere further comprises 0.1-10 mM L-glutamine supplemented to the media. In another embodiment, the composition comprising a discosphere further comprises 0.1-5 mM L-glutamine supplemented to the media. In another embodiment, the composition comprising a discosphere further comprises 5-10 mM L-glutamine supplemented to the media. In another embodiment, the composition comprising a discosphere further comprises 5-8 mM L-glutamine supplemented to the media. In another embodiment, the composition comprising a discosphere further comprises 0.5-2.5 mM L-glutamine supplemented to the media. In another embodiment, the composition comprising a discosphere further comprises 1.5-3 mM L-glutamine supplemented to the media. In another embodiment, the composition comprising a discosphere further comprises 0.5-1.5 mM L-glutamine supplemented to the media. In another embodiment, the composition comprising a discosphere further comprises 0.8-1.2 mM L-glutamine supplemented to the media.

In another embodiment, the composition comprising a discosphere further comprises b-mercaptoethanol supplemented to the media. In another embodiment, the composition comprising a discosphere further comprises 0.01-1 mM b-mercaptoethanol supplemented to the media. In another embodiment, the composition comprising a discosphere further comprises 0.01-0.5 mM b-mercaptoethanol supplemented to the media. In another embodiment, the composition comprising a discosphere further comprises 0.5-1 mM b-mercaptoethanol supplemented to the media. In another embodiment, the composition comprising a discosphere further comprises 0.5-0.8 mM b-mercaptoethanol supplemented to the media. In another embodiment, the composition comprising a discosphere further comprises 00.5-0.25 mM b-mercaptoethanol supplemented to the media. In another embodiment, the composition comprising a discosphere further comprises 0.15-0.3 mM b-mercaptoethanol supplemented to the media. In another embodiment, the composition comprising a discosphere further comprises 0.05-0.15 mM b-mercaptoethanol supplemented to the media. In another embodiment, the composition comprising a discosphere further comprises 0.08-0.12 mM b-mercaptoethanol supplemented to the media.

In another embodiment, the composition comprising a discosphere comprises a media comprising Dulbecco's Modified Eagle's Medium (DMEM). In another embodiment, the composition comprising a discosphere comprises a media further comprising DMEM/F12. In another embodiment, the composition comprising a discosphere comprises a media further comprising ESGRO Complete™ Accutase™. In another embodiment, ESGRO Complete™ Accutase™ is a cell detachment solution of proteolytic and collagenolytic enzymes qualified for use for the detachment of stem cells cultured in serum-free conditions with ESGRO Complete™ Clonal Grade Medium. In another embodiment, 1× Accutase™ enzymes in Dulbecco's PBS comprises 0.5 mM EDTA.4Na and 3 mg/L Phenol. In another embodiment, the composition comprising a discosphere comprises a media comprising HEScGRO hES cell medium (Chemicon Temecula, Calif.).

In another embodiment, the present invention provides that discospheres obtained by the methods of the present invention are further expanded. In another embodiment, the present invention provides that discospheres are dissociated by incubation at 37° C. in DMEM/F12 medium supplemented with collagenase. In another embodiment, the present invention provides that the dissociated cells are expanded by replating the same into methylcellulose-based medium.

In another embodiment, the methods of the present invention provide that the medium is supplemented with 8-20% fetal bovine serum (FBS) when growing a disc tissue. In another embodiment, the methods of the present invention provide that the medium is supplemented with 8-20% fetal bovine serum (FBS) when growing a disc tissue in a scaffold. In another embodiment, the medium comprises 30-70% media derived from cultures of primary human foreskin fibroblasts, or a combination thereof. In another embodiment, the methods of the present invention provide that the medium is free of serum when growing disc stem cells, disc progenitor cells, or a combination thereof. In another embodiment, the methods of the present invention provide that the medium is free of a serum replacer when growing disc stem cells, disc progenitor cells, or a combination thereof. In another embodiment, the methods of the present invention provide that the medium is free of FBS when growing disc stem cells. In another embodiment, the methods of the present invention provide that the medium is free of FBS when growing nucleus pulposus stem cells. In another embodiment, the methods of the present invention provide that the medium is free of FBS when growing progenitor cells. In another embodiment, the methods of the present invention provide that the medium is free of FBS when growing nucleus pulposus progenitor cells.

In another embodiment, the methods of the present invention provide that the medium is free of serum or a serum replacer when isolating disc stem cells or disc progenitor cells. In another embodiment, the methods of the present invention provide that the medium is free of serum or a serum replacer when enriching a heterogeneous population of cells for disc stem cells, disc progenitor cells, or a combination thereof. In another embodiment, the methods of the present invention provide that the medium is free of serum or a serum replacer when growing discospheres comprising disc stem cells, disc progenitor cells, or a combination thereof. In another embodiment, the methods of the present invention provide that the medium is free of serum or a serum replacer when expanding a culture comprising disc stem cells, disc progenitor cells, or a combination thereof. In another embodiment, the methods of the present invention provide that the medium is free of serum or a serum replacer when expanding a culture enriched for disc stem cells, disc progenitor cells, or a combination thereof.

In another embodiment, the present invention provides a disc replacement device comprising nucleus pulposus cells. In another embodiment, the present invention provides an artificial disc comprising nucleus pulposus cells. In another embodiment, the disc replacement device is an intervertebral disc replacement device. In another embodiment, an intervertebral disc is located between the concave articular surfaces of the adjacent vertebral body endplates. In another embodiment, the disc replacement device of the present invention permits movements such as flexion, extension, lateral flexion, and rotation. In another embodiment, the disc replacement device of the present invention is used to repair and/or replace injured or damaged intervertebral discs. In another embodiment, the disc replacement device of the present invention provides a prosthetic disc that combines both stability to support the high loads, of the patient's vertebrae and flexibility to provide the patient with sufficient mobility and proper spinal column load distribution.

In another embodiment, the disc replacement device comprises a disc scaffold. In another embodiment, the scaffold comprises a shape memory alloy. In another embodiment, a shape memory alloy may be deformed during its martensitic phase, but will regain its original shape when it is heated above a certain temperature, such as an austenite phase temperature. In another embodiment, a shape memory alloy of the present invention exhibits a superelastic property, thereby able to absorb large deformations without damaging its structure.

In another embodiment, the disc replacement device comprises a rigid body that fits between the vertebrates with a protuberance extending from a vertebral contacting surface and extends into the vertebral body. In another embodiment, the disc replacement device comprises a disc arthroplasty device for replacement of the spinal disk. In another embodiment, the disc replacement device comprises a ball-and-socket to enable rotation. In another embodiment, the disc replacement device comprises an intermediate layer allowing for movement between the upper joint piece and the lower joint piece.

In another embodiment, the disc replacement device comprises two endplates that are anchored to the top and bottom surfaces of the spinal bones. In another embodiment, the disc replacement device comprises two metal endplates that are anchored to the top and bottom surfaces of the spinal bones. In another embodiment, the metal is cobalt-chrome alloy. In another embodiment, the endplates are coated with nucleus pulposus cell adhesion molecules. In another embodiment, the endplates are coated with molecules promoting nucleus pulposus cell growth.

In another embodiment, the disc replacement device comprises ceramics. In another embodiment, the disc replacement device comprises injectable fluids. In another embodiment, the disc replacement device comprises hydrogels. In another embodiment, the disc replacement device comprises a hydrogel core in a flexible, inelastic, woven polyethylene jacket. In another embodiment, the disc replacement device comprises a polyvinyl alcohol material. In another embodiment, the disc replacement device comprises inflatables. In another embodiment, the disc replacement device comprises elastic coils. In another embodiment, the disc replacement device comprises an elongated elastic memory-coiling spiral. In another embodiment, the elongated elastic memory-coiling spiral is made of polycarbonate urethane. In another embodiment, the disc replacement device comprises a one-piece convex surfaced ceramic or metal implant that anchors to the inferior vertebral body as a hemiarthroplasty. In another embodiment, the disc replacement device comprises a balloon-like implant made of polyurethane. In another embodiment, the disc replacement device comprises a protein hydrogel. In another embodiment, the disc replacement device comprises a thermopolymer.

In another embodiment, the disc scaffold comprises an ECM component. In another embodiment, the ECM component is a structural protein. In another embodiment, the disc scaffold comprises collagen. In another embodiment, the structural protein is elastin. In some embodiments, the ECM component is a specialized protein. In another embodiment, the specialized protein is fibrillin. In another embodiment, the specialized protein is fibronectin. In another embodiment, the specialized protein is laminin. In some embodiments, the ECM component is a proteoglycan. In one embodiment, proteoglycans are composed of a protein core to which is attached long chains of repeating disaccharide units termed of glycosaminoglycans (GAGs) forming extremely complex high molecular weight component.

In another embodiment, collagen is collagen type I. In another embodiment, collagen type I comprises [a1(I)]2[a(I)] chains. In another embodiment, collagen type I is derived from skin, tendon, or bone.

In another embodiment, collagen is collagen type II. In another embodiment, collagen type II comprises [a1(II)]3 chains. In another embodiment, collagen type II is derived from cartilage or vitreous humor. In another embodiment, type II collagen fibrils are cross-linked to proteoglycans in the matrix by type 1× collagen.

In another embodiment, collagen is collagen type III. In another embodiment, collagen type III comprises [a1(III)]3 chains. In another embodiment, collagen type III is derived from skin or muscle, and is frequently found with type I.

In another embodiment, collagen is collagen type IV. In another embodiment, collagen type IV comprises [a1(IV)2[a2(IV)] chains. In another embodiment, collagen type IV is derived from basal lamina.

In another embodiment, collagen is collagen type V. In another embodiment, collagen type V comprises [a1(V)][a2(V)][a3(V)] chains. In another embodiment, collagen type V is derived from an interstitial tissue associated with type I collagen.

In another embodiment, collagen is collagen type VI. In another embodiment, collagen type VI comprises [a1(VI)][a2(VI)][a3(VI)] chains. In another embodiment, collagen type VI is derived from an interstitial tissue associated with type I collagen. In another embodiment, type VI collagen consists of relatively short triple-helical regions about 60 nm long separated by globular domains about 40 nm long. In some embodiments, fibrils of pure type VI collagen form a structure similar to beads on a string.

In one embodiment, collagen is collagen type VII. In one embodiment, collagen type VII comprises [a1(VII)]3 chains. In another embodiment, collagen type VII is derived from epithelia.

In another embodiment, collagen is collagen type VIII. In another embodiment, collagen type VIII comprises [a1(VIII)]3 chains. In another embodiment, collagen type VII is derived from endothelial cells.

In another embodiment, collagen is collagen type IX. In another embodiment, collagen type IX comprises [a1(IX)][a2(IX)][a3(IX)] chains. In another embodiment, collagen type IX is derived from cartilage associated with type II collagen.

In another embodiment, collagen is collagen type X. In another embodiment, collagen type X comprises [a1(X)]3 chains. In another embodiment, collagen type X is derived from hypertrophic and mineralizing cartilage.

In another embodiment, collagen is collagen type XI. In another embodiment, collagen type XI comprises [a1(XI)][a2(XI)][a3(XI)] chains. In another embodiment, collagen type XI is derived from cartilage.

In another embodiment, collagen is collagen type XII. In another embodiment, collagen type XII comprises a1(XII) chains. In another embodiment, collagen type XII is derived from sites wherein types I and III collagens are present.

In another embodiment, type I collagen molecules pack together side-by-side, forming fibrils with a diameter of 50-200 nm. In some embodiments, fibrils, adjacent collagen molecules are displaced from one another by 67 nm, about another-quarter of their length. In some embodiments, collagens types I, II, III, and V form rodlike triple helices to via side-by-side interactions.

In another embodiment, the collagen of the present invention is derived from cows. In another embodiment, collagen of the present invention is derived from patient's own fat or hyaluronic acid.

In another embodiment, collagen is a collagen-like substance which has been modified by dissolving collagen in water and modifying the thusly dissolved collagen to render its surface charge effectively more positive than prior to modification. In another embodiment, this material is well known and is disclosed, e.g., in U.S. Pat. No. 4,238,480. In another embodiment, modified collagen is freeze-dried to form a solid mass of gelatin. In some embodiments, the mass of gelatin may be formed in the shape of a rod, strip, film or flake.

In another embodiment, other forms of collagen which are suitable for use in the present invention include Semed F, a collagen preparation manufactured in native fiber form without any chemical or enzymatic modifications, and Semed S, a lyophilized collagen powder extracted from fresh bovine hides. In another embodiment, the Semed F material is a Type I collagen (greater than 95%), while the Semed S is a mixture of Type I and Type III collagen macro-molecules in which the shape and dimension of tropocollagen in its natural helical orientation is retained.

In another embodiment, the concentration of the collagen in the liquid which is to be freeze-dried can range from 0.5-10% and preferably 1-5%, with the lower concentrations forming less dense or discontinuous solids. In another embodiment, at lower concentrations of 0.5 to 1%, the Semed F forms a structure which approximates dense cobwebs.

In another embodiment, native collagen film, wherein the film strength is preserved and the triple-helix structure of the collagen polymer is maintained intact, can also be used, either alone or with a plasticizer incorporated therewith.

In another embodiment, gelatin or other water soluble forms of collagen are utilized. In another embodiment, soluble forms of collagen will readily polymerize at body temperatures to form a stable subcutaneous gel. In another embodiment, when soluble forms of collagen are implanted into the body, the polymerized material will become rapidly populated by nucleus pulposus cells implanted therein and host fibroblasts. In some embodiments, the material becomes vascularized and can remain histologically stable. In another embodiment, the material becomes vascularized and can remain histologically stable for at least 4 months. In another embodiment, the material becomes vascularized and can remain histologically stable for at least 6 months. In another embodiment, the material becomes vascularized and can remain histologically stable for at least 8 months. In another embodiment, the material becomes vascularized and can remain histologically stable for at least 10 months. In another embodiment, the material becomes vascularized and can remain histologically stable for at least 12 months. In another embodiment, the material becomes vascularized and can remain histologically stable for at least 15 months. In another embodiment, the material becomes vascularized and can remain histologically stable for at least 18 months.

In another embodiment, the present invention provides mixtures of the various types of collagen of the invention to obtain the most desirable features of each grade.

In another embodiment, fibronectins are dimers of 2 similar peptides. In another embodiment, each chain of a fibronectins is 60-70 nm long and 2-3 nm thick. In another embodiment, fibronectins contain at least 6 tightly folded domains each with a high affinity for a different substrate such as heparan sulfate, collagen (separate domains for types I, II and III collagens), and fibrin and cell-surface receptors.

In another embodiment, laminin molecule is a heterotrimer assembled from α,β, and γ-chains. In some embodiments, laminins form independent networks and are associated with type IV collagen networks via entactin, and perlecan. In some embodiments, laminins contribute to cell viability, attachment, and differentiation, cell shape and movement, maintenance of tissue phenotype, and promotion of tissue survival.

In another embodiment, proteoglycans comprise chondroitin sulfate and dermatan sulfate chains. In another embodiment, proteoglycans comprise heparin and heparan sulfate chains. In another embodiment, proteoglycans comprise keratan sulfate chains. In another embodiment, proteoglycans are aggrecans, the major proteoglycan in cartilage. In another embodiment, proteoglycans are versican, present in many adult tissues including blood vessels and skin. In another embodiment, proteoglycans are small leucine rich repeat proteoglycans (SLRPs). In another embodiment, SLRPs include decorin, biglycan, fibromodulin, and lumican.

In another embodiment, the extracellular matrix components are morselized. In another embodiment, morselization of the extracellular matrix proteins increases the surface area for nucleus pulposus cells attachment. In another embodiment, morselization of the extracellular matrix proteins increases the surface area for discospheres attachment. In another embodiment, morselization of the extracellular matrix proteins increases the surface area for disc stem cells attachment. In another embodiment, morselization of the extracellular matrix proteins increases the surface area for disc progenitor cells attachment. In another embodiment, morselization of the extracellular matrix proteins increases the surface area thus aiding diffusion of nutrients and waste products to the implant and from the implant. In another embodiment, morselization of the extracellular matrix proteins allows the introduction of nucleus pulposus cells into the disc scaffold through a needle or a small cannula. In another embodiment, morselization of the extracellular matrix proteins allows the introduction of discospheres into the disc scaffold through a needle or a small cannula. In another embodiment, small holes could be drilled into the disc scaffold for cell attachment.

In another embodiment, the present invention provides that the disc scaffold is obtained from an animal or human. In another embodiment, the present invention provides that the disc scaffold is an intervertebral disc with the vertebral endplates left intact. In another embodiment, the present invention provides that the disc scaffold is a rabbit intervertebral disc with the vertebral endplates left intact (Example 3). In another embodiment, the present invention provides that the disc scaffold is a dog intervertebral disc with the vertebral endplates left intact. In another embodiment, the present invention provides that the disc scaffold is a horse intervertebral disc with the vertebral endplates left intact. In another embodiment, the present invention provides that the disc scaffold is a monkey intervertebral disc with the vertebral endplates left intact. In another embodiment, the present invention provides that the disc scaffold is a pig intervertebral disc with the vertebral endplates left intact. In another embodiment, the present invention provides that the disc scaffold is a cow intervertebral disc with the vertebral endplates left intact. In another embodiment, the present invention provides that the disc scaffold comprising collagen further comprises additional material such as ceramics or metals.

In another embodiment, the present invention provides that the disc replacement device comprises nucleus pulposus cells. In another embodiment, the present invention provides that the disc replacement device comprises human nucleus pulposus cells. In another embodiment, the present invention provides that the disc replacement device comprises nucleus pulposus stem cells. In another embodiment, the present invention provides that the disc replacement device comprises nucleus pulposus progenitor cells. In another embodiment, the present invention provides that the disc replacement device comprises discospheres of the present invention.

In another embodiment, the disc replacement device further comprises media. In another embodiment, the media comprises cell culture media of the present invention (Example 3).

In another embodiment, the present invention provides a method of producing an artificial disc, comprising the step of growing discospheres in a disc scaffold. In another embodiment, the present invention provides a method of producing an intervertebral disc replacement device, comprising the step of growing discospheres in a disc scaffold. In another embodiment, discospheres are administered onto a disc scaffold. In another embodiment, discospheres are administered into a layer comprising collagen in the disc scaffold. In another embodiment, discospheres are administered onto a layer comprising collagen in the disc scaffold. In another embodiment, discospheres are injected into a disc scaffold (Example 4). In another embodiment, discospheres are injected onto a disc scaffold. In another embodiment, discospheres are injected into a layer comprising collagen in the disc scaffold. In another embodiment, discospheres are injected onto a layer comprising collagen in the disc scaffold. In another embodiment, the discospheres of the present invention are applied or injected into or onto the disc scaffold together with a composition of the present invention. In another embodiment, the discospheres of the present invention are applied or injected into or onto the disc scaffold together with a DMEM/F12 medium supplemented with 10% FCS.

In another embodiment, the present invention provides a method of producing an intervertebral disc replacement device, comprising the step of growing nucleus pulposus cells in a disc scaffold. In another embodiment, the present invention provides a method of producing a spinal disc tissue, comprising the step of growing discospheres in a disc scaffold, thereby producing a spinal disc tissue. In another embodiment, a spinal disc tissue of the present invention comprises a disc scaffold of the present invention. In another embodiment, a spinal disc tissue of the present invention comprises nucleus pulposus cells of the present invention. In another embodiment, a spinal disc tissue of the present invention comprises a disc scaffold of the present invention. In another embodiment, a spinal disc tissue of the present invention comprises nucleus pulposus cells of the present invention grown on a disc scaffold of the present invention. In another embodiment, a spinal disc tissue of the present invention comprises a disc scaffold of the present invention. In another embodiment, a spinal disc tissue of the present invention comprises matured nucleus pulposus cells derived from discospheres of the present invention attached to a disc scaffold of the present invention. In another embodiment, a spinal disc tissue of the present invention comprises matured nucleus pulposus cells derived from disc stem cells of the present invention attached to a disc scaffold of the present invention. In another embodiment, a spinal disc tissue of the present invention comprises fibroblasts and matured nucleus pulposus cells derived from discospheres of the present invention attached to a disc scaffold of the present invention.

In another embodiment, the present invention provides a method of producing an intervertebral disc replacement device, comprising coating the disc scaffold of the present invention with nucleus pulposus cells growth factors. In another embodiment, the present invention provides a method of producing an intervertebral disc replacement device, comprising coating the disc scaffold of the present invention with nucleus pulposus cells adhesion factors. In another embodiment, the present invention provides a method of producing an intervertebral disc replacement device, comprising coating the disc scaffold of the present invention with nucleus pulposus cells differentiation factors. In another embodiment, the present invention provides a method of producing an intervertebral disc replacement device, comprising placing the disc scaffold of the present invention in a media comprising nucleus pulposus cells growth factors, adhesion factors, and differentiation factors. In another embodiment, the present invention provides a method of producing an intervertebral disc replacement device, comprising placing the disc scaffold of the present invention in a cell culture media comprising nucleus pulposus cells growth factors, adhesion factors, and differentiation factors. In another embodiment, the present invention provides a method of producing an intervertebral disc replacement device, comprising placing the disc scaffold of the present invention in a media comprising DMEM/F12 medium. In another embodiment, the present invention provides a method of producing an intervertebral disc replacement device, comprising placing the disc scaffold of the present invention in a media comprising DMEM/F12 medium and 10% fetal calf serum (FCS) (Example 3).

In another embodiment, the present invention provides a method of producing an intervertebral disc replacement device, comprising incubating the disc scaffold of the present invention in a media of the invention at 35-42° C. In another embodiment, the present invention provides a method of producing an intervertebral disc replacement device, comprising incubating the disc scaffold of the present invention in a media of the invention at 36-38° C. In another embodiment, the present invention provides a method of producing an intervertebral disc replacement device, comprising incubating the disc scaffold of the present invention in a media of the invention at 37° C.

In another embodiment, the present invention provides a method of producing an intervertebral disc replacement device, comprising incubating the disc scaffold of the present invention in a media of the invention while maintaining 4-10% $CO_2$. In another embodiment, the present invention provides a method of producing an intervertebral disc replacement device, comprising incubating the disc scaffold of the present invention in a media of the invention while maintaining 4-8% $CO_2$. In another embodiment, the present invention provides a method of producing an intervertebral disc replacement device, comprising incubating the disc scaffold of the present invention in a media of the invention while maintaining 5% $CO_2$.

In another embodiment, the present invention provides a method of producing an intervertebral disc replacement device, comprising incubating the disc scaffold of the present invention in a media of the invention for 2-12 hours in an incubator. In another embodiment, the present invention provides a method of producing an intervertebral disc replacement device, comprising incubating the disc scaffold of the present invention in a media of the invention for 3-10 hours in an incubator. In another embodiment, the present invention provides a method of producing an intervertebral disc replacement device, comprising incubating the disc scaffold of the present invention in a media of the invention for 6-10 hours in an incubator. In another embodiment, the present invention provides a method of producing an intervertebral disc replacement device, comprising incubating the disc scaffold of the present invention in a media of the invention for 8 hours in an incubator.

In another embodiment, the present invention provides that incubating the disc scaffold of the present invention in a media of the invention in an incubator comprises a step for preparing the disc scaffold before nucleus pulposus cells are applied into or onto the disc scaffold. In another embodiment, the present invention provides that incubating the disc scaffold of the present invention in a media of the invention in an incubator enable nucleus pulposus cells of the invention to adhere, grow and differentiate on the disc scaffold. In another embodiment, the present invention provides that incubating the disc scaffold of the present invention in a media of the invention in an incubator enable discospheres of the invention to adhere, grow and differentiate on the disc scaffold. In another embodiment, the present invention provides that incubating the disc progenitor cells of the present invention in a media of the invention in an incubator enable nucleus pulposus cells of the invention to adhere, grow and differentiate on the disc scaffold. In another embodiment, the present invention provides that incubating the disc scaffold of the present invention in a media of the invention in an incubator enable disc stem cells of the invention to adhere, grow and differentiate on the disc scaffold. In another embodiment, the present invention provides that incubating the disc scaffold of the present invention in a media of the invention in an incubator enable nucleus pulposus cells, disc stem cells, disc progenitor cells, discospheres, or any combination thereof to adhere, grow and differentiate on the disc scaffold.

In another embodiment, the present invention provides that autograft nucleus pulposus cells are harvested, cultured, and injected to the center of a disc scaffold (Example 4). In another embodiment, the present invention provides that allograft nucleus pulposus cells are harvested, cultured, and injected to the center of a disc scaffold. In another embodiment, the present invention provides that xenograft nucleus pulposus cells are harvested, cultured, and injected to the center of a disc scaffold.

In another embodiment, the present invention provides that nucleus pulposus stem cells, nucleus pulposus progenitor cells, discospheres, or a combination thereof are implanted into the disc scaffold to form a living nucleus pulposus. In another embodiment, nucleus pulposus stem cells, nucleus pulposus progenitor cells, discospheres, or a combination thereof obtained from a cell culture are implanted into the disc scaffold to form a living nucleus pulposus.

In another embodiment, disc stem cells are administered onto a disc scaffold. In another embodiment, disc stem cells are administered into a layer comprising collagen in the disc scaffold. In another embodiment, disc stem cells are administered onto a layer comprising collagen in the disc scaffold. In another embodiment, disc stem cells are injected into a disc scaffold. In another embodiment, disc stem cells are injected onto a disc scaffold. In another embodiment, disc stem cells are injected into a layer comprising collagen in the disc scaffold. In another embodiment, disc stem cells are injected onto a layer comprising collagen in the disc scaffold. In another embodiment, the disc stem cells of the present invention are applied or injected into or onto the disc scaffold together with a composition of the present invention. In another embodiment, the disc stem cells of the present invention are applied or injected into or onto the disc scaffold together with a DMEM/F12 medium with 10% FCS.

In another embodiment, the present invention provides a method of producing an intervertebral disc replacement device, comprising the step of growing nucleus pulposus primary cells in a disc scaffold. In another embodiment, disc primary cells are administered onto a disc scaffold. In another embodiment, disc primary cells are administered into a layer comprising collagen in the disc scaffold. In another embodiment, disc primary cells are administered onto a layer comprising collagen in the disc scaffold. In another embodiment, disc primary cells are injected into a disc scaffold. In another embodiment, disc primary cells are injected onto a disc scaffold. In another embodiment, disc primary cells are injected into a layer comprising collagen in the disc scaffold. In another embodiment, disc primary cells are injected onto a layer comprising collagen in the disc scaffold. In another embodiment, the disc primary cells of the present invention are applied or injected into or onto the disc scaffold together with a composition of the present invention. In another embodiment, the disc primary cells of the present invention are applied or injected into or onto the disc scaffold together with a DMEM/F12 medium with 10% FCS.

In another embodiment, the present invention provides a method of producing an intervertebral disc replacement device, comprising the step of collecting the discospheres, disc stem cells, disc progenitor cells, or a mixture thereof from cell culture media of the present invention by methods known to a person with skill in the art and placing the cells in DMEM/F12. In another embodiment, the present invention provides that discospheres, disc stem cells, disc progenitor cells, or a mixture thereof are first washed free of cell-substrate adhesion inhibitory factor. In another embodiment, the present invention provides that discospheres, disc stem cells, disc progenitor cells, or a mixture thereof are first washed free of methylcellulose.

In another embodiment, the present invention provides that washed discospheres, disc stem cells, disc progenitor cells, or a mixture thereof substantially free of cell-substrate adhesion inhibitory factors are placed in a cell culture media. In another embodiment, the present invention provides that washed discospheres, disc stem cells, disc progenitor cells, or a mixture thereof substantially free of cell-substrate adhesion inhibitory factors are placed in DMEM. In another embodiment, the present invention provides that washed discospheres, disc stem cells, disc progenitor cells, or a mixture thereof substantially free of cell-substrate adhesion inhibitory factors are placed in DMEM/F12. In another embodiment, the present invention provides that washed discospheres, disc stem cells, disc progenitor cells, or a mixture thereof substantially free of cell-substrate adhesion inhibitory factors are placed in DMEM/F12 comprising serum.

In another embodiment, discospheres, disc stem cells, disc progenitor cells, or a mixture thereof are introduced to the disc scaffold in a cell culture media of the invention. In another embodiment, discospheres, disc stem cells, disc progenitor cells, or a mixture thereof are introduced to the disc scaffold in a cell culture media comprising recombinant generated morphogenetic proteins. In another embodiment, discospheres, disc stem cells, disc progenitor cells, or a mixture thereof are introduced to the disc scaffold in a cell culture media comprising PDGF. In another embodiment, discospheres, disc stem cells, disc progenitor cells, or a mixture thereof are introduced to the disc scaffold in a cell culture media comprising TGF-β. In another embodiment, discospheres, disc stem cells, disc progenitor cells, or a mixture thereof are introduced to the disc scaffold in a cell culture media comprising EGF/TGF-α. In another embodiment, discospheres, disc stem cells, disc progenitor cells, or a mixture thereof are introduced to the disc scaffold in a cell culture media comprising IGF-I. In another embodiment, discospheres, disc stem cells, disc progenitor cells, or a mixture thereof are introduced to the disc scaffold in a cell culture media comprising βFGF. In another embodiment, discospheres, disc stem cells, disc progenitor cells, or a mixture thereof are introduced to the disc scaffold in a cell culture media comprising hydrogels. In another embodiment, discospheres, disc stem cells, disc progenitor cells, or a mixture thereof are introduced to the disc scaffold in a cell culture media comprising absorbable or non-resorbable synthetic or natural polymers such as but not limited to collagen, fibrin, polyglycolic acid, polylactic acid, or polytetrafluoroethylene. In another embodiment, discospheres, disc stem cells, disc progenitor cells, or a mixture thereof are introduced to the disc scaffold in a cell culture media comprising antibiotics. In another embodiment, discospheres, disc stem cells, disc progenitor cells, or a mixture thereof are introduced to the disc scaffold in a cell culture media comprising anti-inflammatory medication. In another embodiment, discospheres, disc stem cells, disc progenitor cells, or a mixture thereof are introduced to the disc scaffold in a cell culture media comprising immunosuppressive medications.

In another embodiment, the present invention provides that the collagen fibers of the annulus fibrosis are arranged in 5-50 layers or lamella. In another embodiment, the present invention provides that the collagen fibers of the annulus fibrosis are arranged in 10-40 layers or lamella. In another embodiment, the present invention provides that the collagen fibers of the annulus fibrosis are arranged in 20-30 layers or lamella.

In another embodiment, the present invention provides that the fibers of the lamella alternate direction between layers. In another embodiment, the present invention provides that a blunt tipped needle or cannula could be forced through the annulus. In another embodiment, the present invention provides that upon withdraw of the needle, after injecting the transplanted nucleus pulposus ceels or discospheres, the separated fibers of the lamella would return to their normal position, sealing the annulus. In another embodiment, the present invention provides that the needle would be inserted into the anterior or lateral portion of the disc scaffold. In another embodiment, the present invention provides that those skilled in the art will realize that the needle could be directed into the lateral portion of the disc percutaneously with fluourscopic guidance and into the anterior portion of the disc laparoscopically.

In another embodiment, the present invention provides that the recipient of the nucleus pulposus cells of the present invention is the donor. In another embodiment, the present invention provides that the recipient of the nucleus pulposus cells of the present invention may function at least in part as a donor. In another embodiment, the present invention provides that the donor of nucleus pulposus cells of the present invention is a single donor. In another embodiment, the present invention provides that multiple donors provide nucleus pulposus cells of the present invention to a single recipient. In another embodiment, the present invention provides that multiple donors provide nucleus pulposus cells of the present invention to multiple recipients. In another embodiment, the present invention provides that fetal sources are used. In another embodiment, the present invention provides that the donor or donors of the nucleus pulposus cells of the present invention is or are preferably having a familial relationship to the recipient in order to minimize or avoid immunosuppression. In another embodiment, the present invention provides that the donor or donors of the nucleus pulposus cells of the present invention is or are preferably having a familial relationship to the recipient in order to minimize or avoid the need for immunosuppressive substances. In another embodiment, the present invention provides guidelines for tissue procurement including surgical techniques of removal, number of hours between death of the donor and tissue procurement, and testing of the donor for infectious disease, are well known to one of skill in the art.

In another embodiment, the present invention provides that nucleus pulposus cells injected into or onto the disc scaffold deposit extracellular matrix components. In another embodiment, the present invention provides that discospheres injected into or onto the disc scaffold deposit extracellular matrix components of the disc. In another embodiment, the present invention provides that these extracellular matrix components shape the discs' subsequent physiological functions. In another embodiment, the present invention provides that these extracellular matrix components shape the discs' subsequent biomechanical functions. In another embodiment, the present invention provides that by the $2^{nd}$ week of incubation, the disc tissue demonstrates resistance to pressure force. In another embodiment, the present invention provides that by the $3^{rd}$ week of incubation, the disc tissue demonstrates resistance to pressure force. In another embodiment, the present invention provides that resistance to pressure force indicates that the disc is matured. In another embodiment, the present invention provides that resistance to pressure force indicates that the disc acquired tensile properties. In another embodiment, the present invention provides that by the $8^{th}$ week, the disc tissue demonstrates maximal thickness and resistance to compressive forces. In another embodiment, the present invention provides that by the $9^{th}$ week, the disc tissue demonstrates maximal thickness and resistance to compressive forces. In another embodiment, the present invention provides that by the $10^{th}$ week, the disc tissue demonstrates maximal thickness and resistance to compressive forces.

In another embodiment, the present invention provides a method for total disc replacement. In another embodiment, the present invention provides a method for partial disc replacement. In another embodiment, the method for partial disc replacement comprises replacement of the nucleus pulposus.

In another embodiment, the present invention provides that the ruptured disc is removed in a minimally invasive manner through a 10-25 mm paraspinal incision. In another embodiment, the present invention provides that the ruptured disc is removed in a minimally invasive manner through a 10-20 mm paraspinal incision. In another embodiment, the present invention provides that the ruptured disc is removed in a minimally invasive manner through a 15-18 mm paraspinal incision. In another embodiment, the present invention provides that the ruptured disc is removed in a minimally invasive manner through a 16-20 mm paraspinal incision.

In another embodiment, the present invention provides that pre-prepared scaffold is inserted into the disc space. In another embodiment, the present invention provides that pre-prepared scaffold comprising collagen is inserted into the disc space. In another embodiment, the present invention provides that pre-prepared scaffold is inserted into the disc space and expanded to fill the space.

In another embodiment the recipient receives the disc replacement device of the present invention. In another embodiment the recipient receives nucleus pulposus cells of the present invention. In another embodiment the recipient receives local anesthesia. In another embodiment the recipient receives general anesthesia. In another embodiment the precise anesthesia protocol will be determined by one of skill in the art.

In another embodiment a damaged disc is removed from the recipient by methods known to one of skill in the art. In another embodiment, the disc replacement device of the present invention replaces the damaged disc. In another embodiment, a pre-treated disc scaffold of the present invention replaces the damaged disc. In another embodiment, a pre-treated disc scaffold of the present invention comprising collagen replaces the damaged disc. In another embodiment, a pre-treated disc scaffold of the present invention comprising various collagens of the invention replaces the damaged disc. In another embodiment, a pre-treated disc scaffold of the present invention comprising varios ECM components replaces the damaged disc.

In another embodiment, nucleus pulposus cells are administered to a disc scaffold of the present invention after the disc scaffold is surgically placed in the recipient. In another embodiment, the term "nucleus pulposus cells" comprise disc stem cells, disc progenitor cells, discospheres, or a combination thereof. In another embodiment, nucleus pulposus cells are administered via a blunt tipped needle. In another embodiment, nucleus pulposus cells are administered via a cannula. In another embodiment, nucleus pulposus cells are forced through the annulus. In another embodiment, nucleus pulposus cells are administered via a needle inserted into the anterior or lateral portion of the disc. In another embodiment, one skilled in the art will realize the needle could be directed into the lateral portion of the disc percutaneously with fluourscopic guidance and into the anterior portion of the disc laparoscopically.

In another embodiment, nucleus pulposus cells of the present invention are added to the patient's nucleus pulposus. In another embodiment, the patient's disc is removed with standard techniques. In another embodiment, the patient's disc nucleus could be removed with standard enzymatic techniques. In another embodiment, the patient's disc nucleus could be removed with chymopapain. In another embodiment, the patient's disc nucleus could be removed with the aid of a laser. In another embodiment, the patient's disc nucleus could be removed with the aid of a suction device. In another embodiment, the patient's disc nucleus could be removed with the aid of a shaver. In another embodiment, the patient's disc nucleus could be removed with the aid of a any other useful surgical instrument. In another embodiment, if the nucleus is removed the hole in the annulus must be small and closed at the end of the procedure.

In another embodiment, additional therapeutic substances are added to the transplanted nucleus. In another embodiment, additional therapeutic substances are added to the transplanted disc scaffold. In another embodiment, additional therapeutic substances are added to the transplanted disc replacement device of the present invention.

In another embodiment, additional resorbable culture medium is added to the transplanted nucleus. In another embodiment, additional tissue growth or factors are added to the transplanted nucleus. In another embodiment, additional tissue differentiation factors are added to the transplanted nucleus. In another embodiment, additional recombinant generated morphogenetic proteins are added to the transplanted nucleus. In another embodiment, additional PDGF is added to the transplanted nucleus. In another embodiment, additional TGF-β is added to the transplanted nucleus. In another embodiment, additional EGF/TGF-α are added to the transplanted nucleus. In another embodiment, additional IGF-I is added to the transplanted nucleus. In another embodiment, additional FGF is added to the transplanted nucleus. In another embodiment, additional hydrogels are added to the transplanted nucleus. In another embodiment, additional non-resorbable synthetic or natural polymers are added to the transplanted nucleus. In another embodiment, additional collagen is added to the transplanted nucleus. In another embodiment, additional fibrin is added to the transplanted nucleus. In another embodiment, additional polyglycolic acid is added to the transplanted nucleus. In another embodiment, additional polytetrafluoroethylene is added to the transplanted nucleus. In another embodiment, additional antibiotics are added to the transplanted nucleus. In another embodiment, additional anti-inflammatory medications are added to the transplanted nucleus. In another embodiment, additional immunosuppressive medications are added to the transplanted nucleus.

In another embodiment, additional resorbable culture medium is added to the transplanted disc scaffold. In another embodiment, additional tissue growth or factors are added to the transplanted disc scaffold. In another embodiment, additional tissue differentiation factors are added to the transplanted disc scaffold. In another embodiment, additional recombinant generated morphogenetic proteins are added to the transplanted disc scaffold. In another embodiment, additional PDGF is added to the transplanted disc scaffold. In another embodiment, additional TGF-β is added to the transplanted disc scaffold. In another embodiment, additional EGF/TGF-α are added to the transplanted disc scaffold. In another embodiment, additional IGF-I is added to the transplanted disc scaffold. In another embodiment, additional FGF is added to the transplanted disc scaffold. In another embodiment, additional hydrogels are added to the transplanted disc scaffold. In another embodiment, additional non-resorbable synthetic or natural polymers are added to the transplanted disc scaffold. In another embodiment, additional collagen is added to the transplanted disc scaffold. In another embodiment, additional fibrin is added to the transplanted disc scaffold. In another embodiment, additional polyglycolic acid is added to the transplanted disc scaffold. In another embodiment, additional polytetrafluoroethylene is added to the transplanted disc scaffold. In another embodiment, additional antibiotics are added to the transplanted disc scaffold. In another embodiment, additional anti-inflammatory medications are added to the transplanted disc scaffold. In another embodiment, additional immunosuppressive medications are added to the transplanted disc scaffold.

In another embodiment, additional resorbable culture medium is added to the transplanted disc replacement device. In another embodiment, additional tissue growth or factors are added to the transplanted disc replacement device. In another embodiment, additional tissue differentiation factors are added to the transplanted disc replacement device. In another embodiment, additional recombinant generated morphogenetic proteins are added to the transplanted disc replacement device. In another embodiment, additional PDGF is added to the transplanted disc replacement device. In another embodiment, additional TGF-β is added to the transplanted disc replacement device. In another embodiment, additional EGF/TGF-α are added to the transplanted disc replacement device. In another embodiment, additional IGF-I is added to the transplanted disc replacement device. In another embodiment, additional FGF is added to the transplanted disc replacement device. In another embodiment, additional hydrogels are added to the transplanted disc replacement device. In another embodiment, additional non-resorbable synthetic or natural polymers are added to the transplanted disc replacement device. In another embodiment, additional collagen is added to the transplanted disc replacement device. In another embodiment, additional fibrin is added to the transplanted disc replacement device. In another embodiment, additional polyglycolic acid is added to the transplanted disc replacement device. In another embodiment, additional polytetrafluoroethylene is added to the transplanted disc replacement device. In another embodiment, additional antibiotics are added to the transplanted disc replacement device. In another embodiment, additional anti-inflammatory medications are added to the transplanted disc replacement device. In another embodiment, additional immunosuppressive medications are added to the transplanted disc replacement device.

In another embodiment, additional resorbable culture medium is added to the transplanted discospheres, disc stem cells, disc progenitor cells, or a mixture thereof of the present invention. In another embodiment, additional tissue growth or factors are added to the transplanted discospheres, disc stem cells, disc progenitor cells, or a mixture thereof of the present invention. In another embodiment, additional tissue differentiation factors are added to the transplanted discospheres, disc stem cells, disc progenitor cells, or a mixture thereof of the present invention. In another embodiment, additional recombinant generated morphogenetic proteins are added to the transplanted discospheres, disc stem cells, disc progenitor cells, or a mixture thereof of the present invention. In another embodiment, additional PDGF is added to the transplanted discospheres, disc stem cells, disc progenitor cells, or a mixture thereof of the present invention. In another embodiment, additional TGF-β is added to the transplanted discospheres, disc stem cells, disc progenitor cells, or a mixture thereof of the present invention. In another embodiment, additional EGF/TGF-α are added to the transplanted discospheres, disc stem cells, disc progenitor cells, or a mixture thereof of the present invention. In another embodiment, additional IGF-I is added to the transplanted discospheres, disc stem cells, disc progenitor cells, or a mixture thereof of the present invention. In another embodiment, additional FGF is added to the transplanted discospheres, disc stem cells, disc progenitor cells, or a mixture thereof of the present invention. In another embodiment, additional hydrogels are added to the transplanted discospheres, disc stem cells, disc progenitor cells, or a mixture thereof of the present invention. In another embodiment, additional non-resorbable synthetic or natural polymers are added to the transplanted discospheres, disc stem cells, disc progenitor cells, or a mixture thereof of the present invention. In another embodiment, additional collagen is added to the transplanted discospheres, disc stem cells, disc progenitor cells, or a mixture thereof of the present invention. In another embodiment, additional fibrin is added to the transplanted discospheres, disc stem cells, disc progenitor cells, or a mixture thereof of the present invention. In another embodiment, additional polyglycolic acid is added to the transplanted discospheres, disc stem cells, disc progenitor cells, or a mixture thereof of the present invention. In another embodiment, additional polytetrafluoroethylene is added to the transplanted discospheres, disc stem cells, disc progenitor cells, or a mixture thereof of the present invention. In another embodiment, additional antibiotics are added to the transplanted discospheres, disc stem cells, disc progenitor cells, or a mixture thereof of the present invention. In another embodiment, additional anti-inflammatory medications are added to the transplanted discospheres, disc stem cells, disc progenitor cells, or a mixture thereof of the present invention. In another embodiment, additional immunosuppressive medications are added to the transplanted discospheres, disc stem cells, disc progenitor cells, or a mixture thereof of the present invention.

In another embodiment, a matrix formulated disc stem cell preparation loaded with key nutrients is injected into the disc space and will grow into a disc tissue structure over time restoring the damaged disc (Example 4). In another embodiment, a matrix formulated disc stem cell preparation further comprises resorbable culture medium. In another embodiment, a matrix formulated disc stem cell preparation further comprises tissue growth or factors. In another embodiment, a matrix formulated disc stem cell preparation further comprises tissue differentiation factors. In another embodiment, a matrix formulated disc stem cell preparation further comprises recombinant generated morphogenetic proteins. In another embodiment, a matrix formulated disc stem cell preparation further comprises PDGF. In another embodiment, a matrix formulated disc stem cell preparation further comprises TGF-β. In another embodiment, a matrix formulated disc stem cell preparation further comprises EGF/TGF-α. In another embodiment, a matrix formulated disc stem cell preparation further comprises IGF-I. In another embodiment, a matrix formulated disc stem cell preparation further comprises FGF. In another embodiment, a matrix formulated disc stem cell preparation further comprises hydrogels. In another embodiment, a matrix formulated disc stem cell preparation further comprises non-resorbable synthetic or natural polymers. In another embodiment, a matrix formulated disc stem cell preparation further comprises collagen. In another embodiment, a matrix formulated disc stem cell preparation further comprises fibrin. In another embodiment, a matrix formulated disc stem cell preparation further comprises polyglycolic acid. In another embodiment, a matrix formulated disc stem cell preparation further comprises polytetrafluoroethylene. In another embodiment, a matrix formulated disc stem cell preparation further comprises anti-inflammatory medications. In another embodiment, a matrix formulated disc stem cell preparation further comprises antibiotics. In another embodiment, a matrix formulated disc stem cell preparation further comprises immunosuppressive medications.

In another embodiment, the present invention provides a method of treating a subject having a herniated disc, comprising the step of administering to a subject an artificial disc comprising nucleus pulposus cells. In another embodiment, the subject is a human subject. In another embodiment, the subject is a farm animal. In another embodiment, the subject is a pet animal.

In another embodiment, the present invention provides that administering to a subject an artificial disc comprises transplanting to a subject an artificial disc. In another embodiment, the present invention provides that the replacement device comprises processed biological tissues from a single donor. In another embodiment, the present invention provides that the replacement device comprises processed biological tissues from a single donor which is the patient in need of an artificial disc. In another embodiment, the present invention provides that the replacement device comprises processed biological tissues in combination with men made materials. In another embodiment, the present invention provides that the replacement device comprises processed biological tissues in combination with plastic based materials. In another embodiment, the present invention provides that the replacement device comprises processed biological tissues in combination with ceramics. In another embodiment, the present invention provides that the replacement device comprises processed biological tissues in combination with metals.

In another embodiment, the present invention provides a method of treating a subject having a herniated disc. In another embodiment, the present invention provides a method of treating a subject having a degenerative disc disease (DDD). In another embodiment, the present invention provides a method of treating a subject having a DDD at one level in the lumbar spine (from L3-S1). In another embodiment, the present invention provides a method of treating a subject having no more than Grade 1 spondylolisthesis. In another embodiment, the present invention provides a method of treating a subject having more than Grade 1 spondylolisthesis. In another embodiment, the present invention provides a method of treating a subject having no more than Grade 1 spondylolisthesis that have had no relief from pain after at least six months of non-surgical treatment.

In another embodiment, the present invention provides that administering to a subject an artificial disc restores disc height. In another embodiment, the present invention provides that administering to a subject an artificial disc may reduce pain. In another embodiment, the present invention provides that administering to a subject an artificial disc restores movement at the level where it is implanted. In another embodiment, the present invention provides posterolateral annulotomy after discectomy.

EXPERIMENTAL DETAILS SECTION

Materials and Methods

Methylcellulose-Based Medium for Expanding Disc Stem/Progenitor Cells into Discospheres Comprising The methylcellulose-based (medium for expanding discospheres comprising disc stem/progenitor cells contained a base DMEM/F12 medium supplemented with 2% Methylcellulose, 10 µg/ml insulin, 40 nM progesterone, 200 µM putrescine, 100 µg/ml transferrin, 60 nM sodium selenite, 10 ng/ml recombinant FGF2, and 10 ng/ml recombinant EGF.

Methylcellulose-Based Medium for Expanding Discospheres Comprising Disc Stem/Progenitor Cells The Methylcellulose-based medium for expanding discospheres comprising disc stem/progenitor cells contained a base DMEM/F12 medium supplemented with 0.8% Methylcellulose, 5 µg/ml insulin, 20 nM progesterone, 100 µM putrescine, 50 µg/ml transferrin, and 30 nM sodium selenite. 10 ng/ml FGF2 and 10 ng/ml EGFb were added every $3^{th}$ day.

Histochemistry

Hematoxilin-Eosin Staining

Hematoxilin-Eosin staining on disc biopsies obtained from the discs produced by the procedures disclosed in Example 3 were preformed as follows: Formalin fixed paraffin embedded tissue sections (5 µm) were sequentially deparaffinized and rehydrated. Then slides were stained with Harris' haematoxylin for 10 minutes, washed and blue in running tap water for 1 minute, differentiated in acid alcohol (1% hydrochloric acid in 70% alcohol) for 10 seconds, washed and blue in running tap water for 5 minutes, stained with eosin for 4 minutes, and finally washed in tap water, dehydrated through graded alcohol and cleared in xylene.

von Kossa Staining von Kossa Staining on disc biopsies obtained from the discs produced by the procedures disclosed in Example 3 were preformed as follows: Formalin fixed paraffin embedded tissue sections (5 µm) were sequentially deparaffinized and rehydrated. Sections were incubated with 1% silver nitrate solution in a clear glass coplin jar placed under ultraviolet light for 20 minutes. Then sections were rinsed in several changes of distilled water followed by the removal of un-reacted silver with 5% sodium thiosulfate for 5 minutes. Then sections were rinsed in several changes of distilled water and counterstained with nuclear fast red for 5 minutes. Finally, sections were rinsed in several changes of distilled water, dehydrated through graded alcohol and cleared in xylene.

Immunohistochemical Identification of Collagen Type I, Collagen Type II, or Ki67 in Tissue Immunohistochemical staining for collagen type I, collagen type II, or Ki67 on disc biopsies from Example 3 were preformed as follows: Formalin fixed paraffin embedded tissue sections (5 µm) were sequentially deparaffinized, rehydrated, and blocked for endogenous peroxidase activity following a 95° C. degree, 25 minutes antigen retrieval in Trilogy unmasking solution (Cell Marque, Hot Springs Ark.). Slides were biotin blocked, serum blocked and immunostained using a goat ABC Elite Kit (Vector Labs, Burlingame, Calif.) Antibodies to collagen type I (cat. #: 63170, MP Biomedicals, Solon, Ohio), collagen type II (cat. #: MAB 1330, Chemicon, Billerica, Mass.), or Ki67 (cat. #: MAB4062, Chemicon, Billerica, Mass.) were applied at 1:100 dilution for one hour at room temperature. Positive staining was detected with DAB (3,3'-Diaminobenzidene). Immuno-reactivity was visualized with a Bio-Rad confocal microscope and images collected on a computer for later analysis.

Safranin O Staining for Cartilage

This method was used for the detection of cartilage on formalin-fixed, paraffin-embedded tissue sections. The cartilage was stained orange to red, and the nuclei will were stained black. The background was stained green. Weigert's Iron Hematoxylin Solution was prepared from two stock solutions. Stock Solution A: 1 g Hematoxylin, 100 ml 95% alcohol. Stock Solution B: 4 ml 29% Ferric chloride in water, 95 ml distilled water, 1 ml Hydrochloric acid. Equal parts of stock solution were mixed resulting in Weigert's Iron Hematoxylin Solution.

0.1% Safranin O Solution was prepared by mixing 0.1 g Safranin O, C.I. 50240 and 100 ml distilled water. Then slides were deparaffinized and hydrated to distilled water followed by staining the slides with Weigert's iron hematoxylin working solution for 10 minutes. Followed by washing the slides in running tap water for 10 minutes and staining with fast green (FCF) solution for 5 minutes, rinsing quickly with 1% acetic acid solution for 10 seconds, and staining in 0.1% safranin O solution for 5 minutes. Slides were then dehydrated and cleared with 95% ethyl alcohol, absolute ethyl alcohol, and xylene, using 2 changes each, 2 minutes each. Finally slides were mounted using resinous medium.

Example 1

A Method of Growing Discospheres

A biopsy specimen of human nucleus pulposus was minced into pieces approximately 2-3 millimeters in size and transferred to a 50 ml falcon tube containing 30 ml of Phosphate buffered saline (PBS) supplemented with standard antibiotics and antimycotics (standard penicillin/streptomycin solution (GIBCO BRL) in concentration 1:100).

PBS was aspirated and 30 ml of Dulbecco's Modified Eagle Media with F12 (DMEM/F12) medium containing 300 U/ml of Collagenase II solution was added to the 50 ml tube.

The tube was placed in a horizontal position in a shaker incubator at 37° C. at 100 RPM for 2-3 hours until fragments were completely dissociated.

The cell suspension was filtered through a nylon mesh into a 50 ml falcon tube and triturated with a fire-polished pasteur pipette to form a single-cell suspension. A cell count was performed at this point to determine the cell concentration.

The cell suspension was then centrifuged at room temperature for 4 minutes (min) at 400 g, followed by the removal of the supernatant by aspiration.

Cells were resuspended in DMEM/F12 medium supplemented with insulin (10 ug/ml), progesterone (40 nM), putrescine (200 uM), transferrin (100 ug/ml), sodium selenite (60 nM) to a final density of 120,000 cells/ml.

A volume of a 2% solution of methylcellulose in DMEM/F12 medium equal to final volume obtained previously was added to the cell suspension and mixed by vortexing.

Growth factors EGF and FGF2 were added to final concentration 10 ng/ml and mixed again.

Finally, the cell/media suspension was added to 6-well plates at approximately 2 ml/well comprising about 120,000 cells per well, and incubated at 37° C. in 5% CO2. Each well was pre-coated with an anti-adhesive substance (e.g. poly 2-hydroxyethyl methacrylate (#P-3932 Sigma) anti-adhesive coating) according to manufacturer's recommendations.

Growth factors were added every $3^{th}$ day.

After approximately 2 weeks, discospheres had formed in the culture.

Example 2

A Method of Expanding Discospheres Cell Culture

Discospheres obtained by the method disclosed in Example 1 were dissociated by incubation at 37° C. in DMEM/F12 medium supplemented by collagenase II (300 U/ml).

Dissociated cells were expanded in 6-well plates according by passaging the cells using the same plating and culture techniques as described in Example 1.

Example 3

A Method of Obtaining a Spinal Disc Collagen Scaffold (Annulus)

A postmortem (rabbit cadaver) intervertebral disc was removed by dissection with the vertebral endplates left intact. The intervertebral disc sample was soaked in 4 M guanidine thyocyonate for 24 hours at room temperature to remove intradisc biomaterial. After 24 hours, the intradisc biomaterial was liquidfied.

The liquid was aspirated, and the remaining disc scaffold was washed 3 times with room temperature PBS.

At this stage the disc scaffold can be stored in PBS at 4° C. up to one year.

Example 4

A Method of Obtaining an Artificial Disc

The disc scaffold obtained according to the method disclosed in Example 3 was placed in tissue culture vessel and washed 3 times with DMEM/F12 medium with 10% FCS and incubated at 37° C. in 5% CO2 for 8 hours.

Discospheres were pooled from culture and collected in DMEM/F12. Then discospheres were washed free of methylcellulose with DMEM/F12, and suspended in 200 µl DMEM/F12 medium.

The suspended discosphere were injected into the center of the scaffold incubated at 37° C. in 5% CO2 for 8 hours.

The disc tissue culture vessel was then filled with DMEM/F12 medium and incubated at 37° C. in 5% CO2.

The media was changed every $3^{th}$ day.

Results

Nucleus pulposus cells were harvested from a donor patient and prepared as a single cell suspension as described in Example 1. After approximately 2 weeks, discospheres were collected and prepared for injection into the pre-processed rabbit annulus fibrosis. This disc scaffold containing the disc stem cell preparation was then placed in a tissue culture vessel for 3 months. The media was changed every third day. Each day, a downward pressure was applied to each disc tissue to induce biomechanical regulated differentiation programs.

Biomechanical Properties

Disc cells laid down extracellular matrix components of the disc, which in turn, shaped the discs' subsequent physiological and biomechanical functions. By the $3^{rd}$ week, the disc tissue began to demonstrate resistance to pressure force, indicating its maturation and acquisition of tensile properties. By the 10th week, the disc tissue demonstrated maximal thickness and resistance to compressive forces.

Comparative Histology

After 3 months of culture, the disc tissues were removed from culture and sectioned with a cryostat. Basic histological analyses were completed using selected tissue stains and immunohistochemistry.

Figure 2:
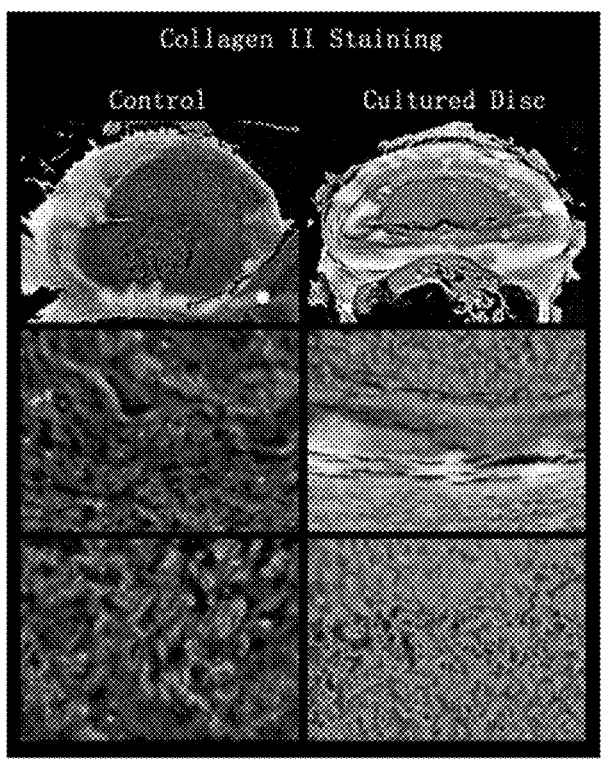
FIG. 2 shows a microscopic histomorphological assessment of the expression of collagen type II in 3-month intervertebral disc cultures after in vitro transplantation of human disc stem cells into evacuated rabbit nucleus pulposus with bony end plates. Photomicrographs of immunostaining for collagen type 2 of (A, C, E) control (rabbit disc tissue) and (B, D, F) cultured intervertebral disc. Magnification: 1.25× (A and B), 10× (C and D), and 20× (E and F). Micrographs C and D demonstrate the transition zone between the inner nucleus pulposus and outer annulus. Micrographs E and F demonstrate the inner zone of the nucleus pulposus and individual nucleus pulposus cells.
Figure 3:
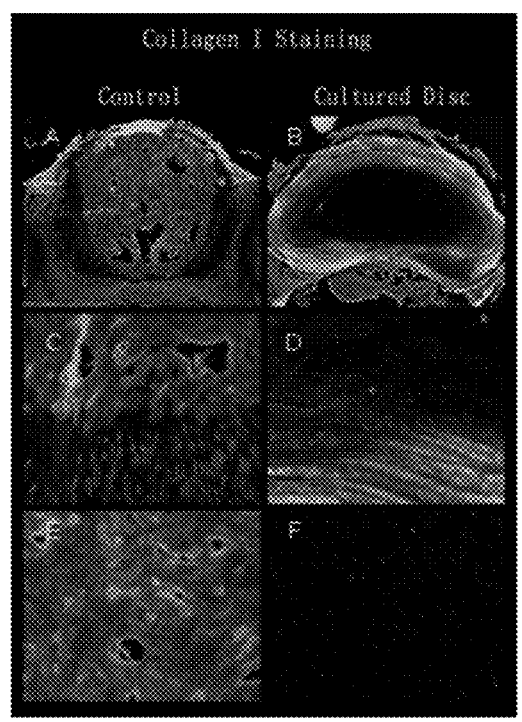
FIG. 3 shows a microscopic histomorphological assessment of the expression of collagen type I in 3 month intervertebral disc cultures after in vitro transplantation of human disc stem cells into evacuated rabbit nucleus pulposus with bony end plates. Photomicrographs of immunostaining for collagen type I of (A, C, E) control (rabbit disc tissue) and (B, D, F) cultured intervertebral disc (annulus matrix prepared in which the nucleus pulposus has been chemically removed and human disc stem cell preparations have been introduced). Magnification: 1.25× (A and B), 10× (C and D), and 20× (E and F). Micrographs C and D demonstrate the transition zone between the inner nucleus pulposus and outer annulus. Micrographs E and F demonstrate the inner zone of the nucleus pulposus and individual nucleus pulposus cells.

As shown in FIG. 1 (Panel 1), Hematoxilin-Eosin staining revealed that the gross structure and cellular morphology of the human disc tissue grown from disc stem cells was comparative to that derived from healthy rabbit disc tissue. Additionally, safranin staining (FIG. 1, Panel 2) demonstrated that a rich cartilage matrix of sulfated proteoglycans was secreted into the extracellular matrix by the disc stem cells and was comparable to healthy rabbit disc tissue at the time of analysis. Von Kossa staining (FIG. 1, Panel 3) demonstrated the absence of any osteogenic differentiation of in vitro disc stem cells in this culture system. Finally, immunohistochemical staining with collagen type II (FIG. 2) and type 1 (FIG. 3) demonstrated high and low expression respectively indicating maturation of the disc tissue and again was found to be comparable to healthy controls.

Demonstration of Lack of Proliferation in the Tissue

Figure 4:
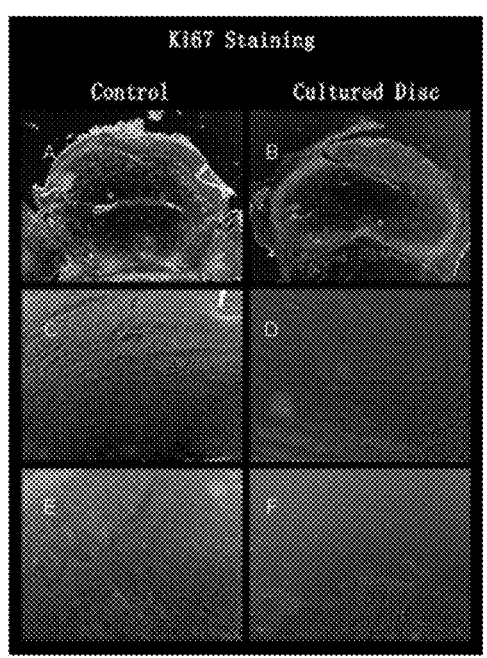
FIG. 4 shows a microscopic histomorphological assessment of the expression of Ki-67 in 3 month intervertebral disc cultures after in vitro transplantation of human disc stem cells into evacuated rabbit nucleus pulposus with bony end plates. Photomicrographs of immunostaining for Ki-67 of (A, C, E) control (rabbit disc tissue) and (B, D, F) cultured intervertebral disc (annulus matrix prepared in which the nucleus pulposus has been chemically removed and human disc stem cell preparations have been introduced). Magnification: 1.25× (A and B), 10× (C and D), and 20× (E and F). Micrographs C and D demonstrate the transition zone between the inner nucleus pulposus and outer annulus. Micrographs E and F demonstrate the inner zone of the nucleus pulposus and individual nucleus pulposus cells.
Figure 5:
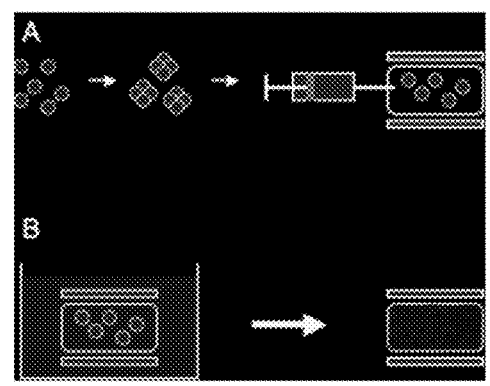
FIG. 5. depicts a schematic of the intervertebral disc culture system with bony end plates. A-Single cell cultures are prepared in media and conditions that promote growth of discospheres (disc stem cell clusters). Discospheres are then prepared and injected into the annulus of a healthy rabbit in which all cells and nucleus pulposus tissue are removed from the disc. B-Intervertebral disc annulus with bony end plates are then put into a culture vessel with media and growth factors. At the end of 3 months, disc stem cells fill the previously empty annulus with a disc like structure.

As a further indicator that the disc tissue was mature and thus did not contain any immature and/or proliferating cells, Ki67 (marker of proliferation) immunostaining was performed on the tissues. As shown in FIG. 4, no proliferating cells were noted in the control tissues or the disc tissue grown from human disc stem cells.

What is claimed is:

1. A method of producing an isolated discosphere, said method comprising:
    (a) culturing nucleus pulposus cells at a density of less than about $1 \times 10^6$ cells/ml in a culture system comprising a serum free medium containing methylcellulose, FGF2, EGF, SCF, IL-6, IL-2, TGF-β, LIF, or a combination thereof that interferes with cell attachment to produce nucleus pulposus stem cells; and (b) allowing the nucleus pulposus stem cells to grow in the culture system to produce a free-floating discosphere comprising a population of disc stem cells.

2. The method of claim 1, wherein said nucleus pulposus cells are human nucleus pulposus cells.

3. The method of claim 1, wherein said serum free media contains EGF.

4. The method of claim 1, wherein said culture system additionally comprises insulin, progesterone, putrescine, transferrin, sodium selenite, or a combination thereof.

5. A method of producing an intervertebral disc repair or restoration device comprising:
   (a) culturing nucleus pulposus cells at a density less than about $1 \times 10^6$ cells/ml in a culture system comprising serum free media containing methylcellulose, FGF2, EGF, SCF, IL-6, IL-2, TGF-β, LIF, or a combination thereof that interferes with cell attachment to produce nucleus Pulposus stem cells;
   (b) allowing the nucleus pulposus stem cells to grow in the culture system to produce a free-floating discosphere comprising a population of disc stem cells;
   (c) isolating the discosphere; and
   (d) applying or injecting the discospheres into or onto a disc scaffold, thereby producing an intervertebral disc repair or restoration device.

6. The method of claim 5, wherein said disc scaffold comprises an extracellular matrix component.

7. The method of claim 5, wherein said serum free media contains EGF.

\* \* \* \* \*